US006889143B2

(12) United States Patent
Behlke et al.

(10) Patent No.: US 6,889,143 B2
(45) Date of Patent: May 3, 2005

(54) METHODS AND SYSTEMS FOR ESTIMATING THE MELTING TEMPERATURE ($T_M$) FOR POLYNUCLEOTIDE MOLECULES

(75) Inventors: Mark Aaron Behlke, Coralville, IA (US); Lingyan Huang, Coralville, IA (US); Richard Owczarzy, Coralville, IA (US); Joseph Alan Walder, Chicago, IL (US)

(73) Assignee: Intergrated DNA Technologies, Inc., Coralville, IN (US)

( * ) Notice: Subject to any disclaimer, the term of this patent is extended or adjusted under 35 U.S.C. 154(b) by 0 days.

(21) Appl. No.: 10/660,253

(22) Filed: Sep. 11, 2003

(65) Prior Publication Data

US 2004/0115705 A1 Jun. 17, 2004

Related U.S. Application Data

(60) Provisional application No. 60/410,663, filed on Sep. 12, 2002.

(51) Int. Cl.[7] .............................................. G06F 17/00
(52) U.S. Cl. ................................ 702/19; 702/20; 435/6
(58) Field of Search .......................... 702/19, 20; 435/6

(56) References Cited

U.S. PATENT DOCUMENTS

| | | | |
|---|---|---|---|
| 5,491,133 A | 2/1996 | Walder et al. | ................. 514/44 |
| 5,510,270 A | 4/1996 | Fodor et al. | ................. 436/518 |
| 5,962,425 A | 10/1999 | Walder et al. | ................. 514/44 |
| 6,197,944 B1 | 3/2001 | Walder et al. | ............. 536/22.1 |

FOREIGN PATENT DOCUMENTS

EP          1 103 910 A1 * 5/2001

OTHER PUBLICATIONS

Le Novère, Bioinformatics 17(12), 1226 (2001).*
Chen et al, Bio Techniques 22(6), 1158 (1997).*
Ahsen et al., Clinical Chemistry 2001, 47:1956–1961 AND Ahsen Supplement.
Blake & Delcourt (Nucl. Acids Res. 1998), 26:3323–3332.
Bloomfield et al., Nucleic Acids: Structure, Properties, and Functions (University Science Books, Sausalito California 2000): pp. 307–308.
Bond et al., Biophysical Journal 1994, 67:825–836.
Breslauer et al., Proc. Natl. Acad. Sci. U.S.A. 1986, 83:3746–3750.
Caruthers et al., Methods Enzymol. 1992, 211:3–20.
Cooper, Curr. Opinion Chem. Biol., 1999, 3:557–563.
Corrigendum, Nucl. Acids Res. 1999, No. 3.
Denhardt, Biochem. Biophys. Res. Commun. 1966, 23:641–646.
DeRisi et al., Science 1997, 278:680–686.
Doktycz et al., Biopolymers 1992, 32:849.
Frank–Kamenetskii, Biopolymers 1971, 10:2623–2624.
Henegarin et al., Biotechniques 1997, 23(3):504–11.
http://www.idtdna.com/program/techbulletins/calculating Molar Extinction Coefficient.asp.
Ivanov & AbouHaidaar, Analytical Biochemistry 1995, 232:249–251.
Kleppe et al., J. Mol. Biol. 1971, 56:341–361.
Lockhart et al.,. Nature Biotech. 1996, 14:1675.
Markouatos et al., J. Clin. Lab Anal. 2002, 16(1):47–51.
Meinkoth & Wahl, Anal. Biochem. 1984, 138:267–284.
Owczarzy et al., Biopolymers 1997, 44:217–239.
Owen et al., Biopolymers 1969, 7:503–516.
Peyret N. (2000) Prediction of Nucleic Acid Hybridization: Parameters and Algorithm, Ph.D. Thesis, Wayne State University, Detroit, Michigan.
Plum & Breslauer, Curr. Opinion truct. Biol. 1995, 5:682–690.
Rouzina & Bloomfield, Biophysical Journal 1999, 77:3242–3251.
Rychlik et al., Nucleic Acids Res. 1990, 18:6409–6412.
Saiki et al., Science 1985, 230:1350–1354.
SantaLucia et al., Biochemistry 1996, 35:3555–3562.
SantaLucia, Proc. natl. Acad. Sci. U.S.A. 1998, 95:1460–1465.
Schena et al., Science 1995, 270:467–470.
Schildkraut et al., Biopolymers 1965, 3:195–208.
Warshaw et al., J. Mol. Biol. 1966, 20:29–38.
Wetmur, Critical Review in Biochemistry and Molecular Biology 1991, 26:227–259.

* cited by examiner

*Primary Examiner*—James Martinell
(74) *Attorney, Agent, or Firm*—Darby & Darby

(57) ABSTRACT

The invention relates to methods and systems for predicting or estimating the melting temperature of duplex nucleic acids, particularly duplexes of oligonucleotides which may be used, for example, as primers or probes in PCR and/or hybridization assays. The invention also relates to methods and systems for designing and selecting oligonucleotide probes and primers having a predicted melting temperature which is optimized for such assays. To this end, algorithms and methods are provided for predicting the melting temperature of a nucleic acid having a predetermined sequence. These methods and algorithms estimate the melting temperature of a nucleic acid duplex under particular salt conditions. The methods and algorithms use novel formulas, having terms and coefficients that are functions of the particular nucleotide sequence, to estimate the effect of particular salt conditions on the melting temperature. As such, the methods and systems of the invention provide superior result compared to existing methods, which do not consider sequence dependent effects of changing salt conditions.

31 Claims, No Drawings

METHODS AND SYSTEMS FOR ESTIMATING THE MELTING TEMPERATURE ($T_M$) FOR POLYNUCLEOTIDE MOLECULES

CROSS-REFERENCE TO RELATED APPLICATIONS

Priority is claimed under 35 U.S.C. 119(e) to U.S. provisional application Ser. No. 60/410,663 filed on Sep. 12, 2002, the entire contents of which is incorporated herein by reference, in its entirety.

FIELD OF THE INVENTION

The present invention relates to methods for the design, analysis and/or evaluation of nucleic acid molecules, particular oligonucleotide nucleic acids (also referred to as "oligomers"). The invention also relates to the design, analysis and/or evaluation of nucleic acids for particular uses or applications. For example, in particular embodiments the invention relates to methods for designing oligonucleotide probes and primers, e.g., for use in PCR or on microarrays. The invention still further relates to systems, including computer systems and computer program products which may be used to practice the particular methods of this invention and/or to program a computer to implement such methods.

BACKGROUND OF THE INVENTION

Hybridization between complementary nucleic acids is an implicit feature in the Watson-Crick model for DNA structure that is exploited for many applications of the biological and biomedical arts. For example, virtually all methods for replicating and/or amplifying nucleic acid molecules are initiated by a step in which a complementary oligonucleotide (typically referred to as a "primer") hybridizes to some portion of a "target" nucleic acid molecule. A polymerase then synthesizes a complementary nucleic acid from the primer, using the target nucleic acid as a "template". See, Kleppe et al., *J. Mol. Biol.* 1971, 56:341–361.

One particular application, known as the polymerase chain reaction (PCR), is widely used in a variety of biological and medical arts. For a description, see Saiki et al., *Science* 1985, 230:1350–1354. In PCR, two or more primers are used that hybridize to separate regions of a target nucleic acid and its complementary sequence. The sample is then subjected to multiple cycles of heating and cooling, repeatedly hybridizing and dissociating the complementary strands so that multiple replications of the target nucleic acid and its complement are performed. As a result, even very small initial quantities of a target nucleic acid may be enormously increased or "amplified" for subsequent uses (e.g., for detection, sequencing, etc.).

Multiplex PCR is a particular version of PCR in which several different primers are used to amplify and detect a plurality of different nucleic acids in a sample—usually ten to a hundred different target nucleic acids. Thus, the technique allows a user to simultaneously amplify and evaluate large numbers of different nucleic acids simultaneously in a single sample. The enormous benefits of high throughput, speed and efficiency offered by this technique has made multiplex PCR increasingly popular. However, achievement of successful multiplex PCR usually involves empirical testing as existing computer programs that pick and/or design PCR primers have errors. In multiplex PCR, the errors become additive and therefore good results are seldom achieved without some amount of trial and error. Markouatos et al., *J. Clin. Lab Anal.* 2002, 16(1):47–51; Henegarin et al., *Biotechniques* 1997, 23(3):504–11.

Other techniques that are widely used in the biological and medical arts exploit nucleic acid hybridization to detect target nucleic acid sequences in a sample. See, for example, Southern, *J. Mol. Biol.* 1975, 98:503–517; Denhardt, *Biochem. Biophys. Res. Commun.* 1966, 23:641–646; Meinhoth & Wahl, *Anal. Biochem.* 1984, 138:267–284. For instance, Southern blotting and similar techniques have long been used in which nucleic acid molecules from a sample are immobilized onto a solid surface or support (e.g., a membrane support). A target nucleic acid molecule of interest may then be detected by contacting one or more complementary nucleic acids (often referred to as a nucleic acid "probes") and detecting their hybridization to nucleic acid molecules on the surface or support (for example, through a signal generated by some detectable label on the probes).

Similar techniques are also known in which one or more nucleic acid probes are immobilized onto a solid surface or support, and a sample of nucleic acid molecules is hybridized thereto. Nucleic acid arrays, for example, are known and have become increasingly popular in the art. See, e.g., DeRisi et al., *Science* 1997, 278:680–686; Schena et al., *Science* 1995, 270:467–470; and Lockhart et al., *Nature Biotech.* 1996, 14:1675. See also, U.S. Pat. No. 5,510,270 issued Apr. 23, 1996 to Fodor et al. Nucleic acid arrays typically comprise a plurality (often many hundreds or even thousands) of different probes, each immobilized at a defined location on the surface or support. A sample of nucleic acids (for example, an mRNA sample, or a sample of cDNA or cRNA derived therefrom) that are preferably detectably labeled may then be contacted to the array, and hybridization of those nucleic acids to the different probes may be assessed, e.g., by detecting labeled nucleic acids at each probe's location on the array. Thus, hybridization techniques using nucleic acid arrays have the potential for simultaneously detecting a large number of different nucleic acid molecules in a sample, by simultaneously detecting their hybridization to the different probes of the array.

The successful implementation of all techniques involving nucleic acid hybridization (including the exemplary techniques described, supra) is dependent upon the use of nucleic acid probes and primers that specifically hybridize with complementary nucleic acids of interest while, at the same time, avoiding non-specific hybridization with other nucleic acid molecules that may be present. For a review, see Wetmur, *Critical Reviews in Biochemistry and Molecular Biology* 1991, 26:227–259. These properties are even more critical in techniques, such as multiplex PCR and microarray hybridization, where a plurality of different probes or primers is used, each of which is preferably specific for a different target nucleic acid.

Duplex stability between complementary nucleic acid molecules is frequently expressed by the duplex's "melting temperature" ($T_m$). Roughly speaking, the $T_m$ indicates the temperature at which a duplex nucleic acid dissociates into single-stranded nucleic acids. Preferably, nucleic acid hybridization is performed at a temperature slightly below the $T_m$, so that hybridization between a probe or primer and its target nucleic acid is optimized, while minimizing non-specific hybridization of the probe or primer to other, non-target nucleic acids. Duplex stability and $T_m$ are also important in applications, such as PCR, where thermocycling may be involved. During such thermocycling steps, it is important that the sample temperature be raised sufficiently above the $T_m$ so that duplexes of the target nucleic acid and its complement are dissociated. In subsequent steps of reannealing, however, the temperature must be brought sufficiently below the $T_m$ that duplexes of the target nucleic acid and primer are able to form, while still remaining high enough to avoid non-specific hybridization events. For a general discussion, see Rychlik et al., *Nucleic Acids Research* 1990, 18:6409–6412.

Traditionally, theoretical or empirical models that relate duplex stability to nucleotide sequence have been used to predict or estimate melting temperatures for particular nucleic acids. For example, Breslauer et al. (*Proc. Natl. Acad. Sci. U.S.A.* 1986, 83:3746–3750) describe a model for predicting melting temperatures that is widely used in the art, known as the "nearest neighbor model". See also, SantaLucia et al., *Biochemistry* 1996, 35:3555–3562; and SantaLucia, *Proc. Natl. Acad. Sci. U.S.A.* 1998, 95:1460–1465. Such models are usually calibrated or optimized for particular salt conditions, typically 1 M $Na^+$. However, applications that exploit nucleic acid hybridization may be implemented in a variety of different salt conditions, with cation concentrations typically being on the order of magnitude of 10–100 mM. Thus, melting temperatures for particular probes or primers in an assay are typically predicted by predicting a melting temperature at a first salt concentration using the nearest neighbor or other model, and then using another theoretical or empirical model to predict what effect(s) the salt conditions of the particular assay will have on that melting temperature.

Most, if not all of the existing models used to estimate $T_m$ treat the effects of salt concentration as being separate from and independent of the nucleotide sequence. For example, Schildkraut et al. (*Biopolymers* 1965, 3:195–208) proposed the following formula to estimate nucleic acid melting temperatures at different sodium ion concentrations, $[Na^+]$:

$$T_m([Na^+])=T_m^0+16.6\times\log[Na^+] \quad \text{(Equation 1.1)}$$

where $T_m^0$ is the melting temperature of the DNA duplex in 1 M sodium ions. Equation 1.1, above, is based on empirical data from the specific study of *Escherichia coli* genomic DNA in buffer of between 0.01–0.2 M $Na^+$. Nevertheless, the use of this equation has been routinely generalized to model any DNA duplex oligomer pair. See, for example, Rychlik et al., *Nucleic Acids Res.* 1990, 18:6409–6412, Ivanov & AbouHaidar, *Analytical Biochemistry* 1995, 232:249–251; Wetmur, *Critical Review in Biochemistry and Molecular Biology* 1991, 26:227–259.

There is evidence, however, indicating that the effects of salt concentration on the melting temperature of nucleotide duplexes are not sequence independent but, rather, depend substantially on sequence composition of the particular nucleic acids. For a review see, Bloomfield et al., *Nucleic Acids: Structure, Properties, and Functions* (University Science Books, Sausalito California 2000): pages 307–308. For example, Owen et al. (*Biopolymers* 1969, 7:503–516) have proposed one empirical formula, based on melting experiments of bacterial DNA, that relates melting temperature ($T_m$) of long polymeric DNAs to $\log[Na^+]$ and the nucleic acid's G-C content, $f(G$-$C)$:

$$f(G\text{-}C)=\tan(70.077+3.32\times\log[Na^+])\times(T_m-175.95)+26 \quad \text{(Equation 1.2)}$$

Still others (Frank-Kamenetskii, *Biopolymers* 1971, 10:2623–2624) have reanalyzed the same experimental data and suggested simplified equations, purportedly reflecting the linear dependence of melting temperature on $\log[Na^+]$:

$$T_m=176.0-(2.60-f(G\text{-}C))\times(36.0-7.04\times\log[Na^+]) \quad \text{(Equation 1.3)}$$

Doktycz et al. (*Biopolymers* 1992, 32:849–864) have applied Equation 1.3, above, to estimate the salt dependence of $T_m$ for average G-C and A-T base pairs in a DNA duplex, and concludes that the dependence is governed by different equations for each type of base pair. Blake & Delcourt (*Nucl. Acids Res.* 1998, 26:3323–3332; Corrigendum, *Nucl. Acids Res.* 1999, 27, No.3) also report that the rate at which $T_m$ changes as a linear function of $\log[Na^+]$ varies with each nearest neighbor, based on melting curves of synthetic tandemly repeating nucleic acid inserts in recombinant pN/MCS plasmids. However, their experiments were conducted in the narrow range of $Na^+$ concentrations from 34 mM to 114 mM.

Rouzina & Bloomfield (*Biophysical Journal* 1999, 77:3242–3251) have also analyzed melting data from large, polymeric DNA molecules and propose an alternative interpretation for the salt dependence of melting temperatures. In particular, the publication suggests a new explanation of empirical Frank-Kamenetskii's relationship (Equation 1.3) that salt dependence of $T_m$ may be due to small differences between the heat capacities of duplex and single-stranded nucleic acid molecules in solution. The publication suggests that this effect may be at least partially sequence dependent. Yet, no new relationship between nucleotide sequence and the effect is proposed or suggested.

Finally, Owczarzy et al., *Biopolymers* 1997, 44:217–239 describe experiments evaluating melting temperatures for oligonucleotide duplexes with various G-C content, $f(G$-$C)$. However, melting temperatures were evaluated at only two concentrations of sodium ions, 1 M and 115 mM. Consequently, the publication provides an equation that only predicts $T_m$ values between those two conditions.

Despite the existence of such data, sequence-independent formulas such as Equations 1.1, supra, are still used in the art to estimate salt-corrected melting temperatures. For instance, as recently as 1998 SantaLucia et al. (*Proc. Natl. Acad. Sci. U.S.A.* 1998, 95:1460–1465) have advocated formulas that estimate salt dependence of a melting temperature by assuming the effects are sequence independent. Thus, even though there may be data suggesting that the effects of salt on a nucleic acid's melting temperature depend on the nucleotide sequence, the available data is incomplete and, in many instances, obtained under conditions which are, at best, remote from those of biological or biomedical techniques that involve nucleic acid hybridization. Specifically, effects of sodium ions on $T_m$ have been systematically studied only for long DNA polymers and DNA dumbbells. See Blake & Delcourt, *Nucl. Acids Res.* 1998, 26:3323–3332 and Doktycz et al. (*Biopolymers* 192, 32:849–864). As a result, the exact effect salt conditions will have on a probe or primer's melting temperature in such assays remains poorly characterized and unknown. Consequently, currently available methods for estimating melting temperatures of particular probe or primer sequences in hybridization assays are inaccurate and unreliable.

Yet, given the prevalence and importance of such assays in the biological and biomedical arts, there is a significant need for methods of estimating and predicting melting temperatures with improved accuracy. In particular, there is a need for methods which predict or estimate the melting temperature for a nucleic acid, particularly for an oligonucleotide (e.g., an oligonucleotide probe or primer) in a PCR or other assay that involve nucleic acid hybridization. There exists, moreover, a need for reliable and accurate methods that estimate effects of changing salt concentration on the melting temperature of particular nucleic acid sequences. There further exists a need for methods of designing oligonucleotides, e.g., as probes or primers for a particular hybridization, PCR or other method, in which the melting temperature of each oligonucleotide is optimized for the particular method or assay.

The citation or discussion of any reference in this section or elsewhere in the specification is made only to clarify the description of the present invention and is not an admission that any such reference is "prior art" against any invention described herein.

SUMMARY OF THE INVENTION

Applicants have discovered a method for estimating a melting temperature for a polynucleotide and its complementary sequence in a particular salt condition. The method is directed to obtaining a reference melting temperature at a reference salt concentration and then calculating, from the reference temperature in a manner that is dependent on the G-C content of the polynucleotide, a new salt dependent "corrected" melting temperature. The invention provides a novel method for reliably estimating melting temperatures for polynucleotides at a desired salt concentration. The method is straightforward and is computationally tractable.

Accordingly, a skilled artisan can readily use the method to estimate polynucleotide melting temperatures under particular salt conditions and/or adjust salt conditions for an assay. In addition, a skilled artisan can readily use the method to estimate melting temperatures for a variety of different polynucleotide probes and/or primers in desired salt conditions and those probes and/or primers having optimal melting temperatures may then be selected.

The method therefore provides for obtaining a reference melting temperature for a particular nucleic acid at a reference salt concentration. Accordingly, a skilled artisan can readily use theoretical, empirical or semi-empirical methods to obtain an accurate or reliable reference melting temperature. The method also provides for a desired salt concentration. A skilled artisan will readily obtain a desired salt concentration based upon the polynucleotide melting conditions of interest to the artisan. More specifically, the method provides for using the reference polynucleotide melting temperature to estimate or determine a salt-dependent, "corrected" melting temperature in a manner that is dependent on the G-C content of the polynucleotide. It is further provided that the G-C content can be used by a skilled artisan to determine a G-C content value.

The method of the present invention provides for the use of formulas which may be used to implement the method of the invention. The formulas elucidate the relationship of the reference melting temperature, the desired salt concentration and the G-C content value in the estimation of the salt "corrected" melting temperature. Accordingly a skilled artisan may readily estimate the desired melting temperature of a polynucleotide using the method of the present invention. In addition, optimized coefficients derived from experimentally measured data are provided for use with the formulations.

Computer systems are also provided that may be used to implement the analytical methods of the invention, including methods of estimating a salt-corrected melting temperature of a polynucleotide. These computer systems comprise a processor interconnected with a memory that contains one or more software components. In particular, the one or more software components include programs that cause the processor to implement steps of the analytical methods described herein. The software components may comprise additional programs and/or files including, for example, sequence or structural databases of polymers.

Computer program products are further provided, which comprise a computer readable medium, such as one or more floppy disks, compact discs (e.g., CD-ROMS or RW-CDS), DVDs, data tapes, etc., that have one or more software components encoded thereon in computer readable form. In particular, the software components may be loaded into the memory of a computer system and may then cause a processor of the computer system to execute steps of the analytical methods described herein. The software components may include additional programs and/or files including databases, e.g., of polymer sequences and/or structures.

BRIEF DESCRIPTION OF DRAWINGS

FIG. 1A shows a UV-melting curve for a 2 $\mu$M solution of the oligonucleotide 5'-TAACCATACTGAATACCTTTTGACG-3' (SEQ ID NO: 45) and its complement dissolved in 68.9 mM Na$^+$ buffer.

FIG. 1B shows a differential scanning calorimetry (DSC) curve for a 90 $\mu$M solution of the oligonucleotide 5'-TAACCATACTGAATACCTTTTGACG-3' (SEQ ID NO:45) and its complement dissolved in 68.9 mM Na$^+$ buffer.

FIG. 2 shows an exemplary computer system that may be used to implement the analytical methods of the invention.

FIG. 3 shows the slope obtained for each of a plurality of different oligomers (SEQ ID NOS:1–80) whose experimentally determined melting temperatures ($T_m$'s) are fit to a linear function of log[Na+], plotted as a function of each oligomer's G-C content $f$(G-C). Melting temperatures for each oligomer were measured in sodium cation concentrations of 68.9, 220, 621 and 1020 mM and are set forth in Table I, infra.

FIG. 4 shows the slopes, as a function of G-C content $f$(G-C), obtained where the inverse of experimentally determined melting temperatures (i.e. $1/T_m$) for each of the plurality of different oligomers (SEQ ID NOS:1–80) are fit to a linear function of log[Na+] utilizing Equation 6.2, infra.

DETAILED DESCRIPTION OF THE INVENTION

Definitions:

The term "melting profile" refers to a collection of measurements of an oligonucleotide and its complement which indicate the oligonucleotide molecule's transition from double-stranded to single-stranded nucleic acid (or vice-versa). The transition of a nucleic acid from double-stranded to single-stranded is often described in the art as the "melting" of that nucleic acid molecule. The transition may also be described as the "denaturation" or "dissociation" of the nucleic acid. Accordingly, a melting profile of the present invention may also be referred to as a "dissociation profile", a "denaturation profile", a "melting curve", a "dissociation curve", etc.

The term "salt concentration" is interchangeably used with the term "ion concentration" and refers, specifically, to the concentration of cations (i.e., positively charged ions within a sample). Types of ions include, but are not limited to, lithium, potassium, sodium, rubidium, cesium and francium. Ions may carry a single or multiple charge. A preferred embodiment of the invention is the use of monovalent ions. It is preferred that the ion concentration ranges from about 1 mM to about 5 M. It is more preferred, however, that the ion concentration range from about 5 mM to about 2 M. In particularly preferred embodiments, the ion concentration ranges from about 70 mM to about 1020 mM.

The "melting temperature" or "$T_m$" of a nucleic acid molecule generally refers to the temperature at which a polynucleotide dissociates from its complementary sequence. Generally, the $T_m$ may be defined as the temperature at which one-half of the Watson-Crick base pairs in duplex nucleic acid molecules are broken or dissociated (i.e., are "melted") while the other half of the Watson-Crick base pairs remain intact in a double stranded conformation (i.e., the fraction of broken based pairs, θ(T)=0.5 when T=$T_m$). In preferred embodiments where duplex nucleic acid molecules are oligonucleotides and in other embodiments where the duplex nucleic acids dissociate in a two-state fashion, the $T_m$ of a nucleic acid may also be defined as the temperature at which one-half of the nucleic acid molecules in a sample are in a single-stranded conformation while the other half of the nucleic acid molecules in that sample are in a double-stranded conformation. $T_m$, therefore defines a midpoint in the transition from double-stranded to single-stranded nucleic acid molecules (or, conversely, in the transition from single-stranded to double-stranded nucleic acid molecules).

It is well appreciated in the art that the transition from double-stranded to single-stranded nucleic acid molecules does not occur at a single temperature but, rather, over a range of temperatures. Nevertheless, the $T_m$ provides a convenient measurement for approximating whether nucleic acid molecules in a sample exist in a single-stranded or double-stranded conformation. As such, the melting temperature of a nucleic acid sample may be readily obtained by simply evaluating a melting profile for that sample.

The methods and algorithms of this invention involve calculating estimated melting temperatures for complementary nucleic acids and can be applied generally to any of the various types of nucleic acids, including but not limited to DNA, RNA, mRNA, cDNA, and cRNA, as well as "protein nucleic acids" (PNA) formed by conjugating bases to an amino acid backbone. Polynucleotides that may be used in accordance with the present invention also include double stranded DNA and RNA duplex oligomers, single stranded DNA and RNA, as well as backbone modifications thereof (for example, methylphosphonate linkages). This also includes nucleic acids containing modified bases, for example, thio-uracil, thio-guanine and fluoro-uracil.

The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.) and alkylators to name a few. The polynucleotides may be derivatized by formation of a methyl or ethyl phosphotriester or an alkyl phosphoramidite linkage. Furthermore, the polynucleotides herein may also be modified with a label capable of providing a detectable signal, either directly or indirectly. Exemplary labels include radioisotopes, fluorescent molecules, biotin and the like.

As used herein, the terms "polynucleotide" and "oligonucleotide" are interchangeable and are generally used to describe nucleic acid polymers typically having no more than about 500 base pairs. In preferred embodiments, the present invention is practiced using oligonucleotides between about 5 and 150 nucleotides in length, and more preferably between about 10 and 30 nucleotides in length. Oligonucleotides used in the present invention may hybridize to any type of nucleic acid from any source; including but not limited to genomic DNA, mRNA, cDNA, Expressed Sequence Tags (ESTs), and chemically synthesized nucleic acids. Oligonucleotides of the invention may also hybridize to other oligonucleotide molecules.

Oligonucleotides and other polynucleotides can be labeled, e.g., with $^{32}$P-nucleotides or nucleotides to which a label, such as biotin or a fluorescent dye (for example, Cy3 or Cy5) has been covalently conjugated. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A pair of hybridized polynucleotides may be complementary along their entire length or, alternatively, along only a part of their sequence. In preferred embodiments, all of the nucleotides in a pair of hybridized oligonucleotides are complementary. However, mismatch base pairing between complementary nucleic acids may occur, and such nucleic acids are therefore said to be less than 100% complementary. In particular, the extent of complementarity is usually indicated by the fraction (e.g., the percentage) of mismatched base pairs out of the total number of base pairs in the complementary polynucleotides. It is very preferred that there is at least 99% complementarity between the polynucleotide and its complementary sequence. However, less complementarity may be acceptable or even desirable in some embodiments. For example, in some embodiments, the level of complementary may be as low as 95%, 85% or 75%.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

Hybridization requires that the two nucleic acids contain complementary sequences. However, mismatches between bases are possible depending on the stringency of the hybridization conditions. The appropriate stringency for hybridizing nucleic acids depends on the length of the nucleic acids and the degree of complementarity, variables well known in the art. The greater the degree of similarity or homology between two nucleotide sequences, the greater the value of $T_m$ for duplexes of nucleic acids having those sequences. For duplexes of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides. Unless other conditions are specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

Nucleic acids can be purified by precipitation, chromatography (including preparative solid phase chromatography), oligonucleotide hybridization, ultracentrifugation, and other means. In one method, nucleic acids are purified using polyacrylamide gel purification (PAGE) techniques. In another preferred embodiment, they are purified using high pressure liquid chromatography (HPLC). Such methods of purification are also well known in the art.

General Methods:

In accordance with the invention, there may be employed conventional molecular biology, microbiology and recombinant DNA techniques within the skill of the art. Such techniques are explained fully in the literature. See, for example, Sambrook, Fitsch & Maniatis, *Molecular Cloning: A Laboratory Manual*, Second Edition (1989) Cold Spring Harbor Laboratory Press, Cold Spring Harbor, N.Y. (referred to herein as "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins, eds. 1984); *Animal Cell Culture* (R. I. Freshney, ed. 1986); *Immobilized Cells and Enzymes* (IRL Press, 1986); B. E. Perbal, *A Practical Guide to Molecular Cloning* (1984); F. M. Ausubel et al. (eds.), *Current Protocols in Molecular Biology*, John Wiley & Sons, Inc. (1994).

This invention pertains to a method for predicting the melting temperature at a specific ion concentration for a polynucleotide having a certain G-C content. This invention can be applied to the design of oligonucleotide probes, hybridization and PCR methods, and microarray hybridization methods.

Overview of the Method:

In accordance with the present invention, methods are provided here for estimating a melting temperature ($T_m$) for a polynucleotide or, more specifically, for a polynucleotide and its complementary sequence. Such methods are particularly well suited for the design of oligonucleotide probes and primers, e.g., for use in biological assays such as PCR and nucleic acid hybridization assays. The methods of the invention are robust and straightforward, and provide reliable predictions or estimations of melting temperatures for polynucleotides under conditions that are typically used in such assays. In particular, using the methods of the invention a skilled artisan may readily determine or estimate melting temperatures for polynucleotides under particular salt conditions and/or may adjust salt conditions for an assay accordingly. Alternatively, the methods of the invention may be used to determine or estimate melting temperatures for a variety of different polynucleotide probes and/or primers in desired salt conditions, and those probes and/or primers having optimal melting temperatures for the assay may then be selected.

In its simplest form, the method of the invention comprises a step of obtaining or determining a "reference" melting temperature for a polynucleotide in a particular salt concentration (i.e., the "reference" salt concentration). The reference temperature may then be used in accordance with the present invention to obtain or estimate a "salt-corrected" melting temperature therefrom. More specifically, the salt-corrected melting temperature may be derived from the reference melting temperature according to a relationship that is dependent upon the polynucleotide's G-C sequence content. A more detailed description of these methods follows below.

Reference melting temperature. A reference melting temperature, typically denoted here by the symbol $T_m^0$, may be readily obtained for a particular nucleic acid using any technique known in the art for obtaining or determining melting temperatures. For example, melting temperatures may be experimentally determined for one or more polynucleotides (as described in the Examples, infra) at some standard or reference salt concentration, and these empirically determined melting temperatures may then be used as reference melting temperatures in accordance with the present invention. However, a reference melting temperature may also be obtained or provided using theoretical, empirical or semi-empirical models that predict melting temperatures at some salt concentration. In particularly preferred embodiments, the reference melting temperature for a polynucleotide is obtained using the "nearest neighbor model", which is well known in the art (see, e.g., Breslauer et al., *Proc. Natl. Acad. Sci. U.S.A.* 1986, 83:3746–3750; and SantaLucia et al., *Proc. Natl. Acad. Sci. U.S.A.* 1998, 95:1460). However, various other models are known in the art and may also be used in accordance with the present invention.

The exact experimental method, model or formula used to obtain the reference melting temperature is not crucial for practicing the invention. For example and as noted above, the reference melting temperature may be determined empirically; e.g., by using the melting temperature of a polynucleotide duplex at some reference salt concentration. However, the melting temperature may also be calculated using some theoretical, empirical or semi-empirical model. The model will preferably provide an 'accurate' or reliable estimate of the melting temperature at some salt concentration for which the model has been optimized. For example, the nearest neighbor model and many other models for predicting melting temperatures use parameters that have been particularly optimized for a 1 M concentration of monovalent cations (specifically, for 1 M Na$^+$). Accordingly, in embodiments where such models are used to obtain a reference melting temperature, the reference salt concentration is preferably 1 M. Generally, those skilled in the art will readily appreciate for what salt concentrations a method or model for obtaining melting temperatures has been optimized and, accordingly, will be able to use those salt concentrations as the "reference" salt concentration (denoted herein by the symbol $[X^+]_0$) for practicing the methods of this invention.

Salt concentration. In accordance with the methods of this invention, the melting temperature of a polynucleotide may be readily determined for a particular salt concentration (denoted $[X^+]$) of interest to a user. Generally, the salt concentration of interest will correspond to salt conditions for a biological assay (e.g. a PCR or hybridization assay) of particular interest to the user. In preferred embodiments of the invention, the salt concentration of interest will be a concentration of sodium ions. However, other monovalent cations (e.g., potassium, lithium, rubidium, cesium and francium) may be substituted for sodium. In many hybridization assays only monovalent cations are present. However, divalent cations such as magnesium may also be present. If divalent cations are present, melting temperatures may be determined using the methods described below for monovalent cations and then adjusted for divalent ion concentrations, e.g., using techniques that are already known in the art. See, for example, Ahsen et al., *Clinical Chemistry* 2001, 47:1956–1961, see also Peyrot N. (2000) "Prediction of Nucleic Acid Hybridization: Parameters and Algorithm," Ph.D. Thesis, Wayne State University, Detroit, Mich.

As demonstrated in the Examples, infra, the methods of the invention are robust, and may be used reliably to determine melting temperatures for a wide range of different salt conditions. Preferred concentrations may be anywhere from about 5 mM to about 2 M, and are more preferably between about 50 mM and 1 M. In particularly preferred embodiments, a salt concentration of interest will be between about 70 and about 1020 mM. However, using empirical techniques that are demonstrated in the below examples, a skilled artisan can readily optimize the formulas and methods of this invention for any salt concentration or range of salt concentrations of interest. Accordingly, the formulas and techniques described here need not be limited to the specific ranges of salt concentration used in those examples.

G-C content value. The invention provides methods and formulas which more accurately estimate salt effects on the melting temperature of a polynucleotide. In particular, these methods adjust the "reference" melting temperature $T_m^0$ in a manner that is dependent upon the polynucleotide's sequence content, specifically the content of guanine (G) and cytosine (C) base pairs that form between a polynucleotide and its complement. Accordingly, the systems and methods of the invention also use a value, referred to herein as the "G-C content value" and denoted by the symbol $f(G-C)$. The G-C content value $f(G-C)$ provides a numerical value which is indicative of the number of G-C base pairs formed between a polynucleotide and its complementary sequence. In preferred embodiments, the G-C content of a polynucleotide may be obtained or provided from the molar fraction of G-C base pairs in the polynucleotide duplex; i.e., $f(G-C)$=(no. G-C base pairs)/(total no. base pairs).

Estimating Salt Dependent Effects of Melting Temperature $(T_m)$:

In accordance with the present invention, Applicants have discovered novel relationships between the melting temperature of a polynucleotide $(T_m)$, the salt concentration $[X^+]$ in which the polynucleotide dissociation (or hybridization) occurs, and the polynucleotide's G-C content value $f(G-C)$. Accordingly, the invention provides novel methods for estimating melting temperatures using these novel relationships. Generally speaking, a "reference" melting temperature $T_m^0$ is obtained or provided for the polynucleotide at a "reference" salt concentration $[X^+]_0$, as described above. The reference melting temperature is then used to calculate a salt-corrected $T_m$ according to a relationship that has been optimized for the polynucleotide's G-C content.

For example, in one preferred embodiment, a salt-corrected melting temperature $(T_m)$ may be estimated or obtained from a reference melting temperature $(T_m^0)$ using the formula:

$$\frac{1}{T_m} = \frac{1}{T_m^0} + k \times \ln\frac{[X^+]}{[X^+]_0} \qquad \text{(Equation 5.1)}$$

In the present invention, the coefficient k is preferably a function of the polynucleotide's G-C content value; i.e., of $f(G-C)$. It is noted that for Equations such as Equation 5.1, as well as for other equations throughout the specification based on the reciprocal of the melting temperature (i.e., $1/T_m$) temperatures should be entered in units of Kelvin. For equations provided in this application that involve $T_m$ (for example, Equation 5.2) units of Kelvin and degrees Celsius may be used interchangeably. Those skilled in the art will be able to readily convert between units of Kelvin and other scales for measuring temperature (e.g. degrees Celsius) using formulas that are well known and routinely used in the art (for example: K=° C.+273.15).

In many embodiments, the relationship provided in Equation 5.1, supra, may be well approximated by a linear function of the reference melting temperature $(T_m^0)$ rather than of its inverse (i.e., $1/T_m^0$). Such a relationship is less computationally intensive than Equation 5.1, and therefore will be simpler to use. Accordingly, the use of such a linear approximation may be preferred, particularly when considering the relatively narrow range of temperatures for which melting temperatures of nucleic acids are typically be considered; i.e., for physiological temperatures, preferably between about 20 and 80° C. (i.e., between about 293 and 353 K).

Accordingly, in another preferred embodiment, a salt-corrected melting temperature $(T_m)$ may be estimated or obtained from a reference melting temperature $(T_m^0)$ using the formula:

$$T_m = T_m^0 + k' \times \ln\frac{[X^+]}{[X^+]_0} \qquad \text{(Equation 5.2)}$$

which is a linear approximation of Equation 5.1, supra. Again, the coefficient k' is preferably a function of the polynucleotide's G-C content value; i.e., of $f(G-C)$.

The coefficient k (or k') is preferably obtained or provided by a formula of the general form:

$$k=k(f(G-C))=m \cdot f(G-C)+k_0 \qquad \text{(Equation 5.3)}$$

In this equation, m and $k_0$ are constant coefficients which may be optimized to determine melting temperatures for polynucleotides having different G-C content under the salt concentration(s) or range of salt concentrations of interest.

For instance, the examples infra describe experiments when appropriate values for these coefficients are optimized for both of Equation 5.1 and 5.2 above, by optimizing the fit quality to melting data for a plurality of polynucleotide sequences. Those skilled in the art will appreciate that the exact value of the coefficients m and $k_0$ will depend on which formula (Equation 5.1 or 5.2) is used to estimate or obtain the salt-corrected melting temperature. Therefore, the coefficients are preferably optimized independently for each formula.

Formulas for estimating or providing a salt-corrected melting temperature (e.g., Equations 5.1 and 5.2, above) may be further optimized by the addition of one or more higher order polynomial term. For example, and not by way of limitation, Equation 5.1 above may be readily modified by the addition of a second order polynomial term, to obtain a formula such as:

$$\frac{1}{T_m} = \frac{1}{T_m^0} + k \times \ln\frac{[X^+]}{[X^+]_0} + b \times (\ln^2[X^+] - \ln^2[X^+]_0) \quad \text{(Equation 5.4)}$$

As before, the coefficient k is preferably a function of the polynucleotide's G-C content value that is optimized for evaluating melting temperatures at the particular salt concentration(s) of interest. As described, supra, (e.g., for Equations 5.1 and 5.2), the coefficient k is preferably obtained or provided by a formula of the general form:

$$k = k(f(G\text{-}C)) = m \cdot f(G\text{-}C) + k_0 \quad \text{(Equation 5.3)}$$

where, again, the coefficients m and $k_0$ may be optimized to determine melting temperatures for polynucleotides under the salt concentration(s) or range of salt concentrations of interest. Again, the exact value of these coefficients should depend on which formula is used to estimate the salt-corrected melting temperature; i.e., the coefficients are preferably optimized independently for each formula.

As another example, Equation 5.2 above may also be readily modified by the addition of a second order polynomial term, to obtain a formula such as:

$$T_m = T_m^0 + k \times \ln\frac{[X^+]}{[X^+]_0} + b \times (\ln^2[X^+] - \ln^2[X^+]_0) \quad \text{(Equation 5.5)}$$

As with the other formulas, the coefficient k is preferably a function of the polynucleotide's G-C content value that is optimized for evaluating melting temperatures at the particular salt concentration(s) or range of salt concentrations of interest; for example, by optimizing the coefficient m and $k_0$ in Equation 5.3, supra. Again, the coefficients are preferably optimized for each formula described in this application.

Equations such as Equation 5.1–5.2 and 5.4–5.5 above may be still further refined by adding additional polynominal terms; e.g., beyond the second order polynomial terms exemplified in Equations 5.4 and 5.5. Thus, for example, embodiments of the invention are also contemplated that may use, e.g., a third order, forth order, and/or even a fifth order polynomial term. Those skilled in the art will be able to modify the equations used in this invention to incorporate still higher order polynomial terms; e.g., using routine formulas and methods well known in the mathematical arts.

Implementation Systems and Methods:

Computer System. The analytical methods described herein can be implemented by the use of one or more computer systems. FIG. 2 schematically illustrates an exemplary computer system suitable for implementation of the analytical methods of this invention. The components of the computer system 201 include processor element 202 interconnected with a main memory 203. The computer system can contain other components such as a mass storage device 204 and user interface devices 205 including for example, example, a monitor, a keyboard, and/or pointing devices 206 like a mouse or other graphical input device. The computer system 201 can be linked to a network 207, which can be part of an Ethernet, a local computer system (e.g., as part of a local area network or LAN), and/or a wide area communication network (WAN) such as the Internet.

Typically, one or more software components are loaded into main memory 203 during operation of computer system 201. Software component 210 represents an operating system, which is responsible for managing computer system 201 and its network connections. Software component 211 represents common languages and functions in the system to assist programs implementing the methods specific to the invention. Equations for practicing the methods of the invention can also be programmed and implemented using any programmable spread sheet software program. Programmable database systems (for example, a SQL database) can be used to program and/or implement the equations and methods of this invention. Thus, software component 212 represents the analytic methods of the invention as programmed in an appropriate procedural language, symbolic package, or the like.

Computer Program Products. The invention also provides computer program products which can be used, e.g., to program or configure a computer system for implementation of analytical methods of the invention. A computer program product of the invention comprises a computer readable medium such as one or more compact disks (i.e., one or more "CDs", which may be CD-ROMs or a RW-CDs), one or more DVDs, one or more floppy disks (including, for example, one or more ZIP™ disks) or one or more DATs to name a few. The computer readable medium has encoded thereon, in computer readable form, one or more of the software components 212 that, when loaded into memory 203 of a computer system 201, cause the computer system to implement analytic methods of the invention. The computer readable medium may also have other software components encoded thereon in computer readable form. Such other software components may include, for example, functional languages 211 or an operating system 210.

System Implementation. In an exemplary implementation, to practice the methods of the invention a G-C content value and/or cation concentration may be loaded into the computer system 201. For example, the G-C content value may be directly entered by a user from monitor and keyboard 205 by directly typing a sequence of symbols representing numbers (e.g., G-C content value). Alternatively, a user may specify a reference ion concentration, e.g., by selecting an ion concentration from a menu of candidate ion concentrations presented on the monitor or by entering an accession number for a ion concentration in a database and the computer system may access the selected ion concentration from the database, e.g., by accessing a database in memory 203 or by accessing the sequence from a database over the network connection, e.g., over the internet.

Finally, the software components of the computer system, when loaded into memory 203, preferably also cause the computer system to estimate a melting temperature according to the methods described herein. For example, the software components may cause the computer system to obtain a reference melting temperature at a particular reference ion concentration for the polynucleotide and then use the reference melting temperature to calculate a modified melting temperature for the polynucleotide utilizing the methods described herein.

Upon implementing these analytic methods, the computer system preferably then outputs, e.g., the melting temperature for the polynucleotide at a desired ion concentration. The output may be output to the monitor, printed on a printer (not shown), written on mass storage 204 or sent through a computer network (e.g., the internet or an intranet such as a Local Area Network) to one or more other computers.

Alternative systems and methods for implementing the analytic methods of this invention are also intended to be comprehended within the accompanying claims. In particular, the accompanying claims are intended to include the alternative program structures for implementing the methods of this invention that will be readily apparent to those skilled in the relevant art(s).

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1
Melting Temperatures of Various Oligomers Measured in Different Salt Conditions:

This example describes experiments in which melting profiles were measured for at least 92 different, exemplary oligonucleotide molecules in various salt concentrations. Melting temperatures are extracted from those profiles for each oligonucleotide at each salt concentration observed, and those melting temperatures are provided in the results, infra. Sequence information for each of the exemplary oligonucleotides is also provided.

Materials and Methods

Oligonucleotide synthesis and purification. DNA oligonucleotides (SEQ ID NOS:1–92) were synthesized using solid phase phosphoramidite chemistry, deprotected and desalted on NAP-5 columns (Amersham Pharmacia Biotech, Piscataway, N.J.) according to routine techniques (Caruthers et al., *Methods Enzymol.* 1992, 211:3–20). The oligomers were purified using 20% polyacrylamide gel electrophoresis in 1×TBE buffer (50 mM Tris, 50 mM boric acid, 1 mM $Na_2EDTA$). The purity of each oligomer was determined by capillary electrophoresis (CE) carried out on a Beckman PACE 5000 (Beckman Coulter, Inc., Fullerton, Calif.). The CE capillaries had a 100 μm inner diameter and contained ssDNA 100R Gel (Beckman-Coulter). Typically, about 0.6 nmole of oligonucleotide was injected into a capillary, ran in an electric field of 444 V/cm and detected by UV absorbance at 260 nm. Denaturing Tris-Borate-7 M-urea running buffer was purchased from Beckman-Coulter.

Compound identity was verified by matrix-assisted laser desorption ionization time-of-light (MALDI-TOF) mass spectroscopy on a Voyager DE™ Biospectometry™ Work station (Applied Biosystems, Foster, Calif.) following the manufacturer's recommended protocol.

Preparation of DNA samples. Melting experiments were carried out in buffer containing 3.87 mM $NaH_2PO_4$, 6.13 mM $Na_2HPO_4$, 1 mM $Na_2EDTA$ and either 50, 100, 200, 600 or 1000 mM NaCl. 1 M NaOH was used to titrate each solution to pH 7.0. Total sodium concentrations were 68.9, 119, 220, 621 and 1020 mM.

The DNA samples were thoroughly dialyzed against melting buffer in a 28-Well Microdialysis System (Invitation Corp., Carlsbad, Calif.) following the manufacturer's recommended protocol. Concentrations of DNA oligomers were estimated from the samples' UV absorbance at 260 nm in a spectrophotometer (Beckman Coulter, Inc., Fullerton, Calif.), using extinction coefficients for each oligonucleotide that were estimated using the nearest neighbor model for calculating extinction coefficients. (See, Warshaw et al., *J. Mol. Biol.* 1966, 20:29–38; See also, http://www.idtdna.com/program/techbulletins/calculating_Molar_Extinction_Coefficient.asp). Oligomer concentrations were estimated at least twice for each sample. If the estimated concentrations for any sample differed more than 4%, the results were discarded and new absorbance measurements were performed.

To prepare oligonucleotide duplexes, complementary DNA oligomers were mixed in 1:1 molar ratio, heated to 367 K (i.e., 94° C.) and slowly cooled to an ambient temperature. Each solution of duplex DNA was diluted with melting buffer to a total DNA concentration ($C_T$) of 2 μM.

Measurement of melting curves. Melting experiments were conducted on a single beam Beckman DU 650 spectrophotometer (Beckman-Coulter) with a Micro $T_m$ Analysis accessory, a Beckman High Performance Peltier Controller (to regulate the temperature), and either 1 cm or 1 mm path-length cuvettes. Melt data were recorded using a PC interfaced to the spectrophotometer. UV-absorbance values at 268 nm wavelength were measured at 0.1 degree increments in the temperature range from 383 to 368 K (i.e., 10–95° C.). Both heating (i.e., "denaturation") and cooling (i.e., "renaturation") transition curves were recorded in each sample at a controlled rate of temperature change (24.9±0.3 Kelvin per hour). Sample temperatures were collected from the internal probe located inside the Peltier holder, and recorded with each sample's UV-absorbance data. Melting profiles were also recorded for samples of buffer alone (no oligonucleotide), and these "blank" profiles were digitally subtracted from melting curves of the DNA samples. To minimize systematic errors, at least two melting curves were collected for each sample in different cuvettes and in different positions within the Peltier holder.

Determination of melting temperatures. To determine each sample's melting temperature, the melting profiles were analyzed using methods that have been previously described (see, Doktycz et al., *Biopolymers* 1992, 32:849–864; Owczarzy et al., *Biopolymers* 1997, 44:217–239). Briefly, the experimental data for each sample was smoothed, using a digital filter, to obtain a plot of the sample's UV-absorbance as a function of its temperature. The fraction of single-stranded oligonucleotide molecules, θ, was then calculated from that plot. The "melting temperature" or "$T_m$" of a sample was defined as the temperature where θ=0.5.

Results:

To evaluate the effects of changing salt concentration on an oligonucleotide's melting temperature ($T_m$), a plurality of different oligonucleotide molecules (also referred to as "oligomers") were synthesized and melting profiles were obtained for each oligomer under different salt conditions. The term "melting profile" refers to a collection of measurements of an oligonucleotide and its complement which indicate the oligonucleotide molecule's transition from double-stranded to single-stranded nucleic acid (or vice-versa). The transition of a nucleic acid from double-stranded to single-stranded is often described in the art as the "melting" of that nucleic acid molecule. The transition may also be described as the "denaturation" or "dissociation" of the nucleic acid. Accordingly, a melting profile of the present invention may also be referred to as a "dissociation profile", a "denaturation profile", a "melting curve", a "dissociation curve", etc.

It is well known in the art that a sample of double-stranded nucleic acid molecules will absorb less UV-light than an equivalent sample of single-stranded nucleic acid molecules. Thus, in one preferred embodiment a melting profile may comprise a collection of measurements indicating the UV absorption of a nucleic acid sample over a range of temperatures. Such a collection of measurements was obtained for the melting profiles in this Example, following the procedures described in Section 6.1.1, supra. In such a melting profile, an increase in UV-absorption as the temperature increases will indicate the extent to which more and more base pairs of duplex nucleic acid molecules in the sample are dissociating and an increasing fraction, θ, of those molecules are present in a single-stranded conformation. Conversely, a decrease in UV-absorption as the temperature decreases indicates that more and more base pairs are forming in the sample so that the fraction of double stranded nucleic acid molecules (1−θ) in the sample is increasing while the fraction of single-stranded nucleic acid molecules (θ) is decreasing.

The "melting temperature" or "$T_m$" of a nucleic acid molecule refers to the temperature above which the nucleic acid may generally be regarded as existing in a single-stranded conformation and below which the nucleic acid may generally be regarded as existing in a double-stranded confirmation. It is well appreciated in the art that the transition from double-stranded to single-stranded nucleic acid molecules does not occur at a single temperature but, rather, occurs over a range of temperatures (e.g., typically a range between about 5 and 15° C.). Nevertheless, the $T_m$ provides a convenient measurement for approximating whether nucleic acid molecule in a sample exist in a single-stranded or double-stranded conformation.

As an example, FIG. 1A shows an exemplary "UV-melting curve" for a 2 μM solution of the oligonucleotide 5'-TAACCATACTGAATACCTTTTGACG-3' (SEQ ID NO:45) and its complement dissolved in 68.9 mM Na⁺ buffer. This "melting curve" was obtained as described in the Material and Method section, supra. Because the solution absorbs more UV-light (260 nm) when the nucleic acid molecules are in a single-stranded conformation then when they are in a double-stranded conformation, the UV-melting curve in FIG. 1A actually monitors the oligonucleotide's transition from the double-stranded to the single-stranded conformation. Inspection of the UV-melting curve reveals that the transition from double to single-stranded conformation does not occur completely at a single temperature, but rather takes place across a range of temperatures. However, this range is very narrow (e.g., between about 5–15° C.). Thus, at temperatures above the center of this transition (e.g., above about 56.5° C. or 329.7 K) the oligonucleotides in this sample can generally be regarded as existing in a single-stranded conformation, whereas at temperatures below that "melting temperature" the oligonucleotides in the sample are generally regarded as existing in a double-stranded conformation (i.e., as "duplex" oligonucleotide).

FIG. 1B shows data from a differential scanning calorimetry (DSC) experiment for a sample of the same oligonucleotide at much higher concentrations (90 μM solution of SEQ ID NO: 45, $C_t$=180 μM, in 68.9 mM Na⁺ buffer). For a detailed description of this experimental technique, see, e.g., Cooper, *Curr. Opinion Chem. Biol.*, 1999, 3:557–563; and Plum & Breslauer, *Curr. Opinion Struct. Biol.*, 1995, 5:682–690.

The plot in FIG. 1B shows the sample's excess heat capacity ($\Delta C_p$) as the temperature is raised from about 293 to about 363 K (i.e., 20° C. to about 90° C.). Heat capacity of the sample increases as the oligonucleotide duplexes in that sample undergo a transition from the double-stranded conformation to the single-stranded conformation. Again, inspection of this figure shows that the transition occurs across a finite but narrow range (e.g., about 5–15 degrees) of temperatures centered at approximately 63° C., where the heat absorption is maximal. Thus, again, at temperatures above about 63° C. (336 K) the oligonucleotides within this sample can generally be regarded as existing in a single-stranded conformation, whereas the oligonucleotides may be generally regarded as existing in a double-stranded conformation at temperatures below about 63° C.

The observation that this transition (from double-stranded to single-stranded DNA) occurs at a higher temperature for the sample in FIG. 1B (approximately 63° C.) than for the sample in FIG. 1A (56.5° C.) may be readily attributed to the higher oligonucleotide concentration in FIG. 1B (180 μM vs. 2 μM) which, as is well known in the art, drives the equilibrium towards the double-stranded nucleic acid conformation.

Generally, the $T_m$ of a nucleic acid may be defined as the temperature at which one-half of the Watson-Crick base pairs in the double-stranded nucleic acid molecules are broken or dissociated (i.e., they are "melted") while the other half of the Watson-Crick base pairs remains intact; i.e., the fraction of broken base pairs, θ(T)=0.5 when T=$T_m$. However, in many cases the transition of oligonucleotides and other nucleic acids considered in this invention is or may be considered as a "two-state" process in which an individual nucleic acid molecule exists either as a duplex nucleic acid with all of its base-pairs intact, or as a single-stranded nucleic acid with no Watson-Crick base pairs between it and its complementary sequence. The fraction of molecules at any given temperature that are partially melted is negligibly small. Accordingly, the fraction θ(T) may be considered as the fraction of single-stranded nucleic acid molecules in a sample of interest, and 1−θ(T) is considered as the fraction of double-stranded nucleic acid molecules in that sample. In such embodiments, the $T_m$ may be equivalently defined as the temperature at which one-half of the nucleic acid molecules are in a single-stranded conformation and one-half of the nucleic acid molecules are in a double-stranded conformation. The exemplary melting and DSC curves shown in FIGS. 1A and 1B, respectively, show that the transition of that oligonucleotide (SEQ ID NO:45) is a two-state process, with only a single transition between two conformation states: double-stranded and single-stranded DNA. The $T_m$ is the temperature at the midpoint of that transition. Thus, the melting temperature of a nucleic acid sample may be readily obtained by evaluating a melting profile for that sample, such as the UV-melting curve illustrated in FIG. 1A or the DSC curve shown in FIG. 1B. See, also, the Materials and Methods Section, supra.

Oligonucleotides corresponding to each of the sequences set forth in SEQ ID NOS:1–92 and their complementary sequences were synthesized and purified according to the methods described in the Materials and Methods section, supra. Capillary electrophoresis assays confirmed that all samples were more than 90% pure, and experimental molar masses of each oligomer were confirmed within 0.4% of their predicted molar mass by mass spectroscopy. For the melting experiments, each of the oligonucleotides listed in Table 1, below (SEQ ID NOS: 1–92) was mixed in a 1:1 molar ratio with its 100% complementary sequence, as described in Material and Methods Section, supra. Melting profiles were then recorded for each oligomer in 68.9, 119, 220, 621 and 1020 mM Na$^+$, and the melting temperature extracted from each profile. The experimentally determined $T_m$ values for each sample were reproducible within 0.3 C.

The $T_m$ values obtained for each oligomer are provided in Table I, below. For convenience, the melting temperatures specified in Table I are listed in units of Kelvin (K), which are preferably used in the implementation of this invention. However, those skilled in the art will be able to readily convert between units of Kelvin and other scales or units for measuring temperature (e.g., degrees Celsius) using formulas that are well known and routinely used in the art (for examples K=° C.+273.15). Sequence information was also recorded for each oligomer, including the total number of bases (N) and the G-C content. Specifically, an oligomer's G-C content $f(G-C)$ is defined here as the fraction of bases that are either guanine or cytosine. Thus, for example, the oligonucleotide set forth in SEQ ID NO:1 comprises a total of 15 bases pairs (i.e., N=15), of which three are either guanine or cytosine. Thus, that particular oligomer's G-C content may be obtained or provided by: $f(G-C)=3/15=0.2$. The nucleotide sequence, total number of base pairs and G-C content for each oligomer are also provided in Table I, along with the corresponding SEQ ID NO.

TABLE I

MEASURED MELTING TEMPERATURES AT VARIOUS [Na$^+$] CONCENTRATIONS

| SEQ ID NO. | Sequence | N | $f$(G-C) | $T_m$ (K) (Total Na$^+$ Concentration) | | | | |
|---|---|---|---|---|---|---|---|---|
| | | | | 68.9 mM | 119 mM | 220 mM | 621 mM | 1020 mM |
| 1 | TACTAACATTAACTA | 15 | 0.20 | 308.5 | 313.7 | 317.3 | 322.5 | 324.3 |
| 2 | ATACTTACTGATTAG | 15 | 0.27 | 311.3 | 314.7 | 318.2 | 323.1 | 324.7 |
| 3 | GTACACTGTCTTATA | 15 | 0.33 | 314.2 | 318.0 | 321.5 | 326.1 | 328.0 |
| 4 | GTATGAGAGACTTTA | 15 | 0.33 | 313.1 | 317.4 | 321.1 | 326.5 | 328.6 |
| 5 | TTCTACCTATGTGAT | 15 | 0.33 | 313.8 | 317.8 | 321.3 | 325.4 | 326.9 |
| 6 | AGTAGTAATCACACC | 15 | 0.40 | 317.5 | 321.0 | 324.8 | 329.4 | 330.3 |
| 7 | ATCGTCTCGGTATAA | 15 | 0.40 | 318.7 | 322.6 | 326.1 | 330.6 | 331.8 |
| 8 | ACGACAGGTTTACCA | 15 | 0.47 | 321.0 | 324.4 | 328.7 | 333.0 | 334.5 |
| 9 | CTTTCATGTCCGCAT | 15 | 0.47 | 323.2 | 327.1 | 330.3 | 334.6 | 335.9 |
| 10 | TGGATGTGTGAACAC | 15 | 0.47 | 319.7 | 324.8 | 327.8 | 332.3 | 333.5 |
| 11 | ACCCCGCAATACATG | 15 | 0.53 | 324.52 | 328.5 | 331.7 | 335.6 | 336.1 |
| 12 | GCAGTGGATGTGAGA | 15 | 0.53 | 324.4 | 328.0 | 331.2 | 334.9 | 336.5 |
| 13 | GGTCCTTACTTGGTG | 15 | 0.53 | 321.0 | 324.8 | 328.3 | 332.3 | 333.5 |
| 14 | CGCCTCATGCTCATC | 15 | 0.60 | 326.0 | 329.9 | 333.3 | 336.8 | 339.0 |
| 15 | AAATAGCCGGGCCGC | 15 | 0.67 | 332.2 | 335.4 | 338.5 | 342.2 | 343.6 |
| 16 | CCAGCCAGTCTCTCC | 15 | 0.67 | 327.3 | 331.2 | 334.7 | 338.3 | 339.9 |
| 17 | GACGACAAGACCGCG | 15 | 0.67 | 331.1 | 334.7 | 337.6 | 340.8 | 341.8 |
| 18 | CAGCCTCGTCGCAGC | 15 | 0.73 | 334.0 | 337.3 | 340.6 | 343.3 | 345.2 |
| 19 | CTCGCGGTCGAAGCG | 15 | 0.73 | 334.7 | 337.8 | 340.3 | 343.2 | 343.9 |
| 20 | GCGTCGGTCCGGGCT | 15 | 0.80 | 338.1 | 340.9 | 343.7 | 347.1 | 347.3 |
| 21 | TATGTATATTTTGTAATCAG | 20 | 0.20 | 317.6 | 320.9 | 325.7 | 330.8 | 334.4 |
| 22 | TTCAAGTTAAACATTCTATC | 20 | 0.25 | 318.9 | 322.7 | 327.1 | 332.6 | 334.7 |
| 23 | TGATTCTACCTATGTGATTT | 20 | 0.30 | 322.3 | 326.7 | 330.6 | 335.5 | 337.6 |
| 24 | GAGATTGTTTCCCTTTCAAA | 20 | 0.35 | 322.5 | 326.0 | 330.8 | 335.8 | 338.5 |
| 25 | ATGCAATGCTACATATTCGC | 20 | 0.40 | 328.4 | 332.7 | 336.1 | 340.2 | 342.1 |

TABLE I-continued

MEASURED MELTING TEMPERATURES AT VARIOUS [Na⁺] CONCENTRATIONS

| SEQ ID NO. | Sequence | N | ƒ(G-C) | $T_m$ (K) (Total Na⁺ Concentration) | | | | |
|---|---|---|---|---|---|---|---|---|
| | | | | 68.9 mM | 119 mM | 220 mM | 621 mM | 1020 mM |
| 26 | CCACTATACCATCTATGTAC | 20 | 0.40 | 324.3 | 327.8 | 331.6 | 335.4 | 337.6 |
| 27 | CCATCATTGTGTCTACCTCA | 20 | 0.45 | 328.8 | 332.7 | 336.4 | 340.5 | 341.7 |
| 28 | CGGGACCAACTAAAGGAAAT | 20 | 0.45 | 326.9 | 331.0 | 334.9 | 339.9 | 341.7 |
| 29 | TAGTGGCGATTAGATTCTGC | 20 | 0.45 | 330.2 | 333.8 | 338.0 | 342.4 | 344.4 |
| 30 | AGCTGCAGTGGATGTGAGAA | 20 | 0.50 | 332.9 | 336.7 | 340.8 | 344.5 | 346.3 |
| 31 | TACTTCCAGTGCTCAGCGTA | 20 | 0.50 | 333.5 | 337.6 | 340.9 | 344.8 | 346.8 |
| 32 | CAGTGAGACAGCAATGGTCG | 20 | 0.55 | 333.0 | 336.7 | 340.2 | 344.3 | 345.7 |
| 33 | CGAGCTTATCCCTATCCCTC | 20 | 0.55 | 329.2 | 333.5 | 337.3 | 341.5 | 343.5 |
| 34 | CGTACTAGCGTTGGTCATGG | 20 | 0.55 | 332.8 | 336.3 | 339.8 | 343.7 | 344.3 |
| 35 | AAGGCGAGTCAGGCTCAGTG | 20 | 0.60 | 337.7 | 340.9 | 344.6 | 348.3 | 349.5 |
| 36 | ACCGACGACGCTGATCCGAT | 20 | 0.60 | 339.2 | 342.3 | 345.8 | 350.0 | 350.5 |
| 37 | AGCAGTCCGCCACACCCTGA | 20 | 0.65 | 339.7 | 343.1 | 347.2 | 350.1 | 351.7 |
| 38 | CAGCCTCGTTCGCACAGCCC | 20 | 0.70 | 340.4 | 343.9 | 347.2 | 350.9 | 351.4 |
| 39 | GTGGTGGGCCGTGCGCTCTG | 20 | 0.75 | 342.4 | 345.9 | 349.4 | 352.8 | 354.2 |
| 40 | GTCCACGCCCGGTGCGACGG | 20 | 0.80 | 344.1 | 347.1 | 350.5 | 353.0 | 354.3 |
| 41 | GATATAGCAAAATTCTAAGTTAATA | 25 | 0.20 | 322.3 | 326.7 | 330.9 | 336.5 | 339.4 |
| 42 | ATAACTTTACGTGTGTGACCTATTA | 25 | 0.32 | 329.8 | 333.9 | 337.9 | 342.8 | 345.0 |
| 43 | GTTCTATACTCTTGAAGTTGATTAC | 25 | 0.32 | 325.9 | 329.3 | 333.8 | 339.3 | 340.9 |
| 44 | CCCTGCACTTTAACTGAATTGTTTA | 25 | 0.36 | 330.7 | 334.6 | 338.8 | 343.3 | 345.7 |
| 45 | TAACCATACTGAATACCTTTTGACG | 25 | 0.36 | 329.7 | 333.4 | 337.5 | 342.1 | 344.5 |
| 46 | TCCACACGGTAGTAAAATTAGGCTT | 25 | 0.40 | 332.5 | 336.3 | 340.5 | 345.0 | 347.0 |
| 47 | TTCCAAAAGGAGTTATGAGTTGCGA | 25 | 0.40 | 332.3 | 336.2 | 340.4 | 344.8 | 347.0 |
| 48 | AATATCTCTCATGCGCCAAGCTACA | 25 | 0.44 | 335.3 | 338.9 | 343.5 | 348.2 | 349.7 |
| 49 | TAGTATATCGCAGCATCATACAGGC | 25 | 0.44 | 334.4 | 337.9 | 342.3 | 346.0 | 348.2 |
| 50 | TGGATTCTACTCAACCTTAGTCTGG | 25 | 0.44 | 332.2 | 336.3 | 340.3 | 344.5 | 346.8 |
| 51 | CGGAATCCATGTTACTTCGGCTATC | 25 | 0.48 | 333.9 | 337.9 | 341.9 | 346.5 | 347.9 |
| 52 | CTGGTCTGGATCTGAGAACTTCAGG | 25 | 0.52 | 335.3 | 339.0 | 342.8 | 347.4 | 348.8 |
| 53 | ACAGCGAATGGACCTACGTGGCCTT | 25 | 0.56 | 341.3 | 345.3 | 349.2 | 352.6 | 354.3 |
| 54 | AGCAAGTCGAGCAGGGCCTACGTTT | 25 | 0.56 | 341.5 | 345.8 | 349.5 | 353.2 | 354.7 |
| 55 | GCGAGCGACAGGTTACTTGGCTGAT | 25 | 0.56 | 340.2 | 344.0 | 347.9 | 351.8 | 353.3 |
| 56 | AAAGGTGTCGCGGAGAGTCGTGCTG | 25 | 0.60 | 342.8 | 346.8 | 350.6 | 354.4 | 355.6 |
| 57 | ATGGGTGGGAGCCTCGGTAGCAGCC | 25 | 0.68 | 343.9 | 347.7 | 351.4 | 354.8 | 356.6 |
| 58 | CAGTGGGCTCCTGGGCGTGCTGGTC | 25 | 0.72 | 345.1 | 348.8 | 352.3 | 355.8 | 356.5 |
| 59 | GCCAACTCCGTCGCCGTTCGTGCGC | 25 | 0.72 | 346.8 | 349.6 | 353.8 | 356.4 | 357.8 |
| 60 | ACGGGTCCCCGCACCGCACCGCCAG | 25 | 0.80 | 350.0 | 353.1 | 357.2 | 360.3 | 361.5 |
| 61 | TTATGTATTAAGTTATATAGTAGTAGTAGT | 30 | 0.20 | 323.9 | 328.2 | 332.5 | 338.3 | 339.8 |

TABLE I-continued

MEASURED MELTING TEMPERATURES AT VARIOUS [Na⁺] CONCENTRATIONS

| SEQ ID NO. | Sequence | N | ƒ(G-C) | $T_m$ (K) (Total Na⁺ Concentration) | | | | |
|---|---|---|---|---|---|---|---|---|
| | | | | 68.9 mM | 119 mM | 220 mM | 621 mM | 1020 mM |
| 62 | ATTGATATCCTTTTCTATTCATCTTTCATT | 30 | 0.23 | 326.7 | 331.5 | 335.5 | 341.8 | 343.6 |
| 63 | AAAGTACATCAACATAGAGAATTGCATTTC | 30 | 0.30 | 331.5 | 335.1 | 339.3 | 344.5 | 346.4 |
| 64 | CTTAAGATATGAGAACTTCAACTAATGTGT | 30 | 0.30 | 330.0 | 334.5 | 338.1 | 343.7 | 345.0 |
| 65 | CTCAACTTGCGGTAAATAAATCGCTTAATC | 30 | 0.37 | 334.0 | 338.0 | 341.9 | 347.6 | 348.7 |
| 66 | TATTGAGAACAAGTGTCCGATTAGCAGAAA | 30 | 0.37 | 334.5 | 338.6 | 342.8 | 348.0 | 349.6 |
| 67 | GTCATACGACTGAGTGCAACATTGTTCAAA | 30 | 0.40 | 335.9 | 340.0 | 344.0 | 349.1 | 350.1 |
| 68 | AACCTGCAACATGGAGTTTTTGTCTCATGC | 30 | 0.43 | 337.7 | 341.5 | 345.7 | 350.9 | 351.9 |
| 69 | CCGTGCGGTGTGTACGTTTTATTCATCATA | 30 | 0.43 | 337.1 | 341.5 | 345.0 | 349.7 | 350.8 |
| 70 | GTTCACGTCCGAAAGCTCGAAAAAGGATAC | 30 | 0.47 | 337.5 | 341.4 | 345.3 | 350.4 | 351.9 |
| 71 | AGTCTGGTCTGGATCTGAGAACTTCAGGCT | 30 | 0.50 | 339.5 | 343.6 | 347.7 | 352.0 | 353.8 |
| 72 | TCGGAGAAATCACTGAGCTGCCTGAGAAGA | 30 | 0.50 | 339.5 | 343.6 | 347.3 | 352.2 | 354.2 |
| 73 | CTTCAACGGATCAGGTAGGACTGTGGTGGG | 30 | 0.57 | 340.8 | 344.9 | 347.9 | 352.1 | 353.3 |
| 74 | ACGCCCACAGGATTAGGCTGGCCCACATTG | 30 | 0.60 | 344.5 | 347.9 | 351.7 | 355.9 | 357.2 |
| 75 | GTTATTCCGCAGTCCGATGGCAGCAGGCTC | 30 | 0.60 | 343.8 | 348.1 | 351.3 | 355.6 | 357.3 |
| 76 | TCAGTAGGCGTGACGCAGAGCTGGCGATGG | 30 | 0.63 | 345.4 | 348.9 | 352.5 | 356.5 | 357.8 |
| 77 | CGCGCCACGTGTGATCTACAGCCGTTCGGC | 30 | 0.67 | 345.9 | 349.5 | 352.7 | 356.6 | 357.7 |
| 78 | GACCTGACGTGGACCGCTCCTGGGCGTGGT | 30 | 0.70 | 347.7 | 351.6 | 354.7 | 358.4 | 359.5 |
| 79 | GCCCCTCCACTGGCCGACGGCAGCAGGCTC | 30 | 0.77 | 349.5 | 353.0 | 356.8 | 360.3 | 360.9 |
| 80 | CGCCGCTGCCGACTGGAGGAGCGCGGGACG | 30 | 0.80 | 351.0 | 354.8 | 357.8 | 360.9 | 361.8 |
| 81 | ATCAATCATA | 10 | 0.20 | 294.5 | 297.7 | 301.1 | 305.6 | 306.8 |
| 82 | TTGTAGTCAT | 10 | 0.30 | 297.8 | 301.0 | 304.4 | 308.0 | 309.2 |
| 83 | GAAATGAAAG | 10 | 0.30 | 295.3 | 298.5 | 302.3 | 306.3 | 307.6 |
| 84 | CCAACTTCTT | 10 | 0.40 | 302.2 | 305.3 | 309.1 | 312.8 | 313.8 |
| 85 | ATCGTCTGGA | 10 | 0.50 | 307.0 | 310.6 | 313.7 | 317.7 | 318.1 |
| 86 | AGCGTAAGTC | 10 | 0.50 | 300.6 | 304.3 | 307.8 | 312.7 | 313.4 |
| 87 | CGATCTGCGA | 10 | 0.60 | 312.4 | 315.5 | 318.8 | 321.6 | 322.3 |
| 88 | TGGCGAGCAC | 10 | 0.70 | 317.6 | 321.1 | 324.5 | 328.2 | 328.5 |
| 89 | GATGCGCTCG | 10 | 0.70 | 317.4 | 320.2 | 323.3 | 326.8 | 326.7 |
| 90 | GGGACCGCCT | 10 | 0.80 | 319.9 | 323.5 | 326.3 | 329.7 | 330.2 |
| 91 | CGTACACATGC | 11 | 0.55 | 313.5 | 316.7 | 319.3 | 322.8 | 323.1 |
| 92 | CCATTGCTACC | 11 | 0.55 | 311.3 | 314.9 | 317.7 | 321.1 | 322.1 |

Example 2

Sequence Dependent Salt Effects on $T_m$

As an initial evaluation of the effect(s) sequence composition and length may have on a nucleic acid's melting temperature $T_m$, the experimentally determined melting temperatures for each oligonucleotide in Table I, supra, were fit in a least squares analysis to each of the following linear regressions:

$$T_m = T_m^\circ + m\log[\text{Na}^+] \qquad \text{(Equation 6.1)}$$

$$\frac{1}{T_m} = \frac{1}{T_m^0} + m\log[\text{Na}^+] \quad \text{(Equation 6.2)}$$

Equations that are similar in form to Equations 6.1 and 6.2 are well known in the art and have been used to predict nucleic acid melting temperatures for specified salt concentrations. However, the versions of these formulas that have been previously described use coefficients (i.e., for m) that are constants and are independent of (and therefore unaffected by) either the nucleic acid's length or base composition. For example, Schildraut et al. (*Biopolymers* 1965, 3:195–208) describe an equation that is similar to Equation 6.1, above, for estimating a nucleic acid's melting temperature as a function of sodium ion concentration:

$$T_m(\text{Na}^+) = T_m(1M) + 16.6 \log[\text{Na}^+] \quad \text{(Equation 6.3)}$$

See also, Rychlik et al., *Nucl. Acids Res.* 1990, 18:6409; Ivanov & AbouHaidar, *Analytical Biochemistry* 1995, 232:249–251; and Wetmur, *Critical Review in Biochemistry and Molecular Biology* 1991, 26:227–259. In the above Equation 6.3, the oligomer's melting temperature in 1 M sodium salt is used as the reference melting temperature (i.e., $T_m^0 = T_m(1M)$). This reference temperature may be measured (e.g., as described above) or it may be calculated or predicted, e.g., by the nearest neighbor model of Breslauer et al., *Proc. Natl. Acad. Sci. U.S.A.* 1986, 83:3746–3750. See also, SantaLucia et al., *Biochemistry* 1996, 35:3555–3562; and Santa Lucia, *Proc. Natl. Acad. Sci. U.S.A.* 1998, 95:1460–1465.

Others have used a formula that is similar to Equation 6.3, above, but using a value of m=12.5 rather than 16.6. (See, SantaLucia et al., *Biochemistry* 1996, 35:3555–3562).

Alternatively, an equation that relates the entropy change of oligonucleotide dissociation, $\Delta S°$, to changing sodium ion concentrations has also been proposed (See, Santa Lucia, *Proc. Natl. Acad. Sci U.S.A.*, 1998, 95:1460–1465):

$$\Delta S° (\text{Na}^+) = \Delta S° (1M) + 0.368N \ln[\text{Na}^+] \quad \text{(Equation 6.4)}$$

where N is the total number of phosphates in the nucleotide duplex divided by two and $\Delta S° (1M)$ is the entropy of dissociation in 1M Na$^+$, which is preferably calculated using an appropriate nearest neighbor model (described above). Equations are also well known in the art that relate the melting temperature, $T_m$, to the enthalpy and entropy of oligonucleotide dissociation ($\Delta H°$ and $\Delta S°$, respectively) and the total oligonucleotide strand concentration, $C_T$ (for example, see Santa Lucia, supra):

$$T_m = \frac{\Delta H^0}{(\Delta S^0 + R\ln C_T/4)} \quad \text{(Equation 6.5)}$$

If it is assumed that the enthalpy of polynucleotide dissociation does not vary in changing salt conditions, then Equations 6.4 and 6.5 above may be readily combined to derive an alternative equation relating $T_m$ to salt concentration:

$$\frac{1}{T_m} = \frac{1}{T_m^0} + \frac{0.368N}{\Delta H^0} \times \ln\frac{[\text{Na}^+]}{[\text{Na}^+]_0} \quad \text{(Equation 6.6)}$$

where standard transition enthalpy, $\Delta H°$, is preferably calculated using an appropriate nearest neighbor model.

None of the equations described above accounts for any content of the particular polynucleotide sequence under consideration. Indeed, existing models of polynucleotide dissociation assume that cations stabilize polynucleotide duplexes by partially neutralizing the negative charges of each strand's phosphate background. (See, Schildkraut et al., *Biopolymers* 1965, 3:195–208; and SantaLucia et al., *Proc. Natl. Acad. Sci* 1998, 95:1460–1465). Such models suggest that any salt effect on polynucleotide dissociation would be sequence independent.

Applicants have determined, however, that the effect(s) of salt concentration on the melting temperature of a nucleic acid is itself dependent on the nucleotide sequence. This discovery is readily apparent from the preliminary analysis described in this example. A coefficient value m was obtained for each oligomer in Table I when its measured melting temperatures are fit to Equation 6.1. The coefficients m thus obtained for each oligonucleotide are plotted in FIG. 3, as a function of the oligomer's G-C content $f(G-C)$. If the effects of changing salt concentration on the melting temperature were in fact sequence independent, as suggested by the prior art and by Equation 6.3, the same coefficient m would be obtained for all oligomers and the data plotted in FIG. 3 would form a horizontal line. However, it is apparent from inspection of FIG. 3 that the coefficient in actually decreases as the G-C content increases.

Data points for oligomers of 15, 20, 25 and 30 base pairs in length are distinctly labeled in FIG. 3. The coefficient m decreases at a similar rate for oligomers of all these different lengths. Thus, these data demonstrate that while the effect of changing salt concentration depends upon the sequence composition of a nucleic acid, it is substantially independent of the nucleic acid's length.

FIG. 4 shows, as a function of the G-C content $f(G-C)$, the coefficient m obtained for each oligomer in Table II when its measured melting temperatures are fit to Equation 6.2, supra. Again, if the effects of changing salt concentration on melting temperature were actually sequence independent (as suggested by formulas used in the prior art) the data plotted in this figure would form a horizontal line. In fact, however, the coefficient m increases linearly with the oligomers' G-C content. As in FIG. 3, the coefficient m changes at a similar rate with G-C content for oligomers of different length. Thus, FIG. 4 also demonstrates that, while the effect of changing salt concentration depends upon the sequence composition of a nucleic acid, the effect is substantially independent of the nucleic acid's length.

Example 3

Formulas for Improved Prediction of $T_m$ for Different Salt Conditions

To evaluate the effect(s) that differing salt concentrations may have on an oligonucleotide's melting temperature, the experimentally determined melting temperatures set forth in Table I, supra, were fit to various different equations that predict melting temperature based on: (1) salt concentration (in this example, [Na$^+$]), and (2) oligonucleotide sequence content (e.g., $f(G-C)$). Generally speaking, the equations were of one of the following forms:

$$T_m = T_m^0 + k(f(G-C)) \times \ln\frac{[\text{Na}^+]}{[\text{Na}^+]_0} + \quad \text{(Equation 6.7)}$$
$$b \times (\ln^2[\text{Na}^+]_{(1)} - \ln^2[\text{Na}^+]_{(0)})$$

$$\frac{1}{T_m} = \frac{1}{T_m^0} + k(f(G-C)) \times \ln\frac{[\text{Na}^+]}{[\text{Na}^+]_0} + \quad \text{(Equation 6.8)}$$
$$b \times (\ln^2[\text{Na}^+] - \ln^2[\text{Na}^+]_{(0)})$$

In Equations 6.7 and 6.8, above, $T_m$ denotes a melting temperature to be determined for a nucleic acid in a particular concentration of monovalent cations, $[Na^+]$. $T_m^0$ denotes the nucleic acid's melting temperature in some "reference" concentration of the monovalent cations $[Na^+]_{(0)}$. Typically, a value of 1 M is selected as the reference concentration (i.e., $[Na^+]_{(0)}=1$ M). However, any value may be selected for a reference concentration and a skilled artisan practicing this invention will readily appreciate when and what other reference concentration values may be used.

The reference melting temperature, $T_m^0$ may be a melting temperature that is experimentally determined (e.g., as described in Section 6.1, above) for the nucleic acid at the reference concentration of cations, $[Na^+]_{(0)}$. However, the value of $T_m^0$ may also be calculated using methods, such as the nearest neighbor model, that are well known and routinely used in the art to determine a nucleic acid's melting temperature at some concentration of cations. For instance, the reference melting temperature $T_m^0$ may be calculated using a nearest neighbor model as described, e.g., by SantaLucia et al., *Proc. Natl. Acad. Sci. U.S.A.* 1998, 95:1460; or, less preferably, Breslauer et al., *Proc. Natl. Acad. Sci. U.S.A.* 1986, 83:3746–3750 (see also, the references cited supra in connection with the nearest neighbor model). Preferably, both the predicted melting temperature $T_m$, and the reference melting temperature $T_m^0$ are specified in Kelvin (K).

In embodiments where a reference melting temperature is calculated from a theoretical model, the parameters of that model will typically have been calibrated, optimized or otherwise selected for a particular concentration of cations (e.g., for 1 M $Na^+$). A skilled artisan practicing the invention will appreciate, therefore, that the reference concentration of cations used in such embodiments (i.e. the value $[Na^+]_{(0)}$ in Equations 6.7 and 6.8, supra) will preferably be that value for which the theoretical model's parameters have been evaluated.

In the present example and in most preferred embodiments of the invention, the monovalent cations are sodium cations. However, use of the symbol for sodium cations (i.e., $Na^+$) in the above equations is done here merely to simplify the description of this invention. The formulas presented here, as well as the algorithms they represent and illustrate, may be used to estimate or predict melting temperature in different concentrations of any monovalent cation, including lithium cations ($Li^+$), potassium cations ($K^+$), rubidium cations ($Rb^+$), cesium cations ($Cs^+$) and francium cations ($Fr^+$) to name a few.

As demonstrated in Example 2, above, the effect of salt concentration on the melting temperature of a nucleic acid is itself dependent on nucleotide sequence. Moreover, Applicants have determined, as demonstrated here, that such sequence-dependent effects may be accounted for when predicting or estimating $T_m$ values, by simply using a coefficient k which is a function of the nucleotide sequence content. In particular and in preferred embodiments of the invention, the coefficient k may be a function of the nucleic acid's G-C content $f(G-C)$.

As used herein to describe the present invention, the G-C content of a nucleic acid, $f(G-C)$, refers to the fraction of that nucleic acid's nucleotide bases that are either guanine (G) or cytosine (C). Thus, for example, the oligomer set forth in SEQ ID NO:1 (see, also, in Table I, supra) comprises a total of 15 bases (i.e., n=15), of which three are either guanine or cytosine. Thus, that oligomer's G-C content may be obtained or provided by: $f(G-C)=3/15=0.2$.

The second term in Equations 6.7 and 6.8 (i.e., the term: $b \times (\ln^2[Na^+]_{(1)} - \ln^2[Na^+]_{(0)})$) is an exemplary second-order polynominal term. In preferred embodiments, the use of this term with an appropriately selected coefficient value b provides for greater accuracy and greater reliability when estimating the melting temperature for a nucleic acid under particular salt conditions.

In still other embodiments, additional higher order polynomial terms may also be used in Equations 6.7–6.8, to estimate salt-corrected melting temperatures with even greater accuracy and reliability. Thus, the invention also contemplates the optional use of third, forth and/or even fifth order polynomial terms. Those skilled in the art will be able to modify the equations used in this invention to incorporate such higher order polynomial terms using routine formulas and methods well known in the mathematical arts.

Those skilled in the art will also recognize that, when higher order polynominal terms are used in these equations, it will be necessary to re-optimize the coefficients for optimal results. Thus, for example, when the second order polynominal term is used in Equation 6.7 and/or 6.8 (i.e., $b \neq 0$) it may be necessary to select a value for the coefficient k which, generally, will be different from the value selected when such higher order polynominal terms are not used (i.e., when b=0).

It is also noted that the formulas provided in Equations 6.7 and 6.8 are set forth with respect to the "natural logarithm" (i.e., a logarithm of the base e=2.1718) of a cation concentration or of a ratio of cation concentrations. As a skilled user will readily appreciate, it may be preferable in many instances to perform calculations using logarithms of a different base (e.g., the logarithm of base 10 or of base 2) which may, for example, be simpler to calculate. The logarithmic terms in Equations 6.7 and 6.8, as well as in the other formulas and equations set forth in this document, may be readily adapted to such other forms by simply making an appropriate adjustment to the coefficient(s); more specifically by multiplying the coefficient(s) by an appropriate factor. Those skilled in the art will be able to readily obtain or determine the appropriate factor(s) and make the necessary adjustment to the logarithmic coefficient(s). Accordingly, it is understood that versions of these equations which use logarithms of other bases are mathematically equivalent to the equations and formulations set forth in this application, and merely provide alternative representations or descriptions of the algorithms and computational methods of this invention. Indeed, those skilled in the mathematical arts will appreciate that the equations and formulas set forth throughout this application may be written or expressed in a variety of different ways that are mathematically equivalent. Such mathematically equivalent expressions merely represent alternative representations or descriptions of the computational methods that they describe rather than any departure from those methods.

Values for the coefficients k and b were selected for Equations 6.7 and 6.8, above, that optimized the fit of experimentally determined $T_m$ values (see, Table I, supra) to those equations. First, the experimentally determined $T_m$ values were fit to a form of those equations in which the optional second order polynominal term (i.e., the term $b \times (\ln^2[Na^+]_{(1)} - \ln^2[Na^+]_{(0)})$) was omitted (i.e., b=0). A coefficient k was selected that is a linear function of the nucleic acid G-C content:

$$k(f(G-C)) = m \cdot f(G-C) + k_0 \qquad \text{(Equation 6.9)}$$

Constant values for the coefficients m and $k_0$ were selected that optimized the goodness of fit. In a second analysis, the experimentally determined $T_m$ values were fit to a form of Equations 6.7 and 6.8 that included the optional second term ($b \neq 0$). The linear form of coefficient k set forth in Equation 6.9 was again used, and constant values for the coefficients m, $k_0$ and b were selected to optimize goodness of fit.

In each analysis, a reference salt concentration of $[Na^+]_{(0)}$=1.02 M was used, and the reference melting temperature, $T_m^{(0)}$ was the oligomer's experimentally determined melting temperature at that cation concentration. Goodness of fit was evaluated from the reduced "chi-square" value ($\chi_r^2 = \chi^2/v$) and from $<|\Delta T_m|>_{AVE}$, the average difference between the measured $T_m$ values and corresponding $T_m$ values predicted using the equation. The chi-squared goodness of fit test compares a theoretical distribution with the observed data from a sample. (See William H. Press et al., *Numerical Recipes in C: The Art of Scientific Computing* 659–61 (2d Ed. 1992)). Thus, smaller values for ($\chi_r^2$ and/or $<|\Delta T_m|>_{AVE}$ indicate that the equation or model used accurately and reliably predicts actual melting temperatures for different salt concentrations.

Coefficient values for each fit of the experimental data in Equations 6.7 and 6.8 are provided in Table II, below, along with each fit's reduced chi-squared and $<|\Delta T_m|>_{AVE}$ values.

TABLE II

Empirical Fits of Experimental $T_m$ Values

| Equation | Coefficient k = m · f(G − C) + $k_0$ | | | Fit Quality | |
|---|---|---|---|---|---|
| | m | $k_0$ | b | $\chi^2/v$ | $<|\Delta T_m|>_{AVE}$ |
| 6.8 | 4.29 × 10⁻⁵ | −3.95 × 10⁻⁵ | 9.40 × 10⁻⁶ | 4.4 | 0.5 |
| 6.7 | −4.62 | 4.52 | −0.985 | 9.9 | 0.7 |
| 6.8 | 3.85 × 10⁻⁵ | −6.18 × 10⁻⁵ | - 0 - | 19.5 | 1.1 |
| 6.7 | −3.22 | 6.39 | - 0 - | 21.8 | 1.2 |

The date from Table I, supra, were also fit to Equations that have been previously described for estimating salt effects on polynucleotide melting temperatures. Each of those formulas is also discussed herein above, in Example 2.

More specifically, the data in Table I were fit to a form of Equation 6.1, supra using a coefficient m=16.6 (described by Schildkraut et al., Biopolymers 1965, 3:195–208) and also to a form of that equation with the coefficients m=12.5 (See, SantaLucia et al., *Biochemistry* 1996, 35:3555–3562). In addition, the data were also fit to Equation 6.6, supra.

As before, each analysis used a reference salt concentration $[Na^+]_{(0)}$=1.02 M. The reference melting temperature, $T_m^{(0)}$ was the oligomer's experimentally determined melting temperature. The enthalpy term in Equation 6.6 (i.e., $\Delta H°$) was calculated for each oligonucleotide using the nearest neighbor model and parameters optimized for 1 M $Na^+$ concentration (SantaLucia et al. *Proc. Natl. Acad. Sci.* 1998, 95:1460–1465).

Goodness of fit was evaluated from the reduced "chi-square" value ($\chi^2 = \chi^2/v$) and from $<|\Delta T_m|>_{AVE}$, the average difference between the measured $T_m$ values and corresponding $T_m$ values predicted using the equation. The reduced chi-squared and $<|\Delta T_m|>_{AVE}$ values for Equations 6.1 and 6.6 are provided in Table III, below.

TABLE III

EMPIRICAL FITS OF EXPERIMENTAL $T_m$ VALUES TO PRIOR ART EQUATIONS

| Equation | $\chi^2/v$ | $<|\Delta T_m|>_{AVE}$ |
|---|---|---|
| 6.6 | 44.3 | 1.7 |
| 6.1 (m = 16.6) | 337.7 | 5.1 |
| 6.1 (m = 12.5) | 68.4 | 2.1 |

These results confirm that melting temperatures of polynucleotides may be more accurately and reliably estimated by using formulas such as Equations 6.7 and 6.8, above, that depend on nucleotide content.

Thus, four new formulas are provided here which relate the melting temperature of a nucleic acid to the salt conditions in which the nucleic acid denaturation is actually performed:

$$T_m = T_m^0 + (6.39 - 3.22 \times f(G-c)) \times \ln \frac{[Na^+]}{[Na^+]_0} \quad \text{(Equation 6.10)}$$

$$\frac{1}{T_m} = \frac{1}{T_m^0} + (3.85 \times f(G-C) - 6.18) \times 10^{-5} \times \ln \frac{[Na^+]}{[Na^+]_0} \quad \text{(Equation 6.11)}$$

$$T_m = T_m^0 + (4.52 - 4.62 \times f(G-C)) \times \ln \frac{[Na^+]}{[Na^+]_0} - \quad \text{(Equation 6.12)}$$
$$0.985 \times \{\ln^2[Na^+] - \ln^2[Na^+]_{(0)}\}$$

$$\frac{1}{T_m} = \frac{1}{T_m^0} + (4.29 \times f(G-C) - 3.95) \times 10^{-5} \times \ln \frac{[Na^+]}{[Na^+]_0} + \quad \text{(Equation 6.13)}$$
$$9.40 \times 10^{-6} \times \{\ln^2[Na^+] - \ln^2[Na^+]_{(0)}\}$$

Any one of these formulas may be used in connection with the present invention, e.g., to predict the melting temperature of a particular nucleic acid in certain salt conditions. Indeed, the data presented in Table II, and Table III supra, shows that these equations and algorithms may predict or estimate the melting temperature of a particular nucleic acid with greater accuracy and reliability than existing methods.

References Cited

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A method for estimating a melting temperature ($T_m$) for a polynucleotide at a desired ion concentration [$X^+$], said polynucleotide having a known G-C content value, $f(G\text{-}C)$, comprising:
   (a) obtaining a reference melting temperature ($T_m^0$) for the polynucleotide, said reference melting temperature being a melting temperature obtained or provided for the polynucleotide at a reference ion concentration [$X^+$]$_0$; and
   (b) modifying the reference melting temperature by a logarithm of the ratio of said desired ion concentration to said reference ion concentration, said logarithm being multiplied by a coefficient which is a function of the G-C content value,
wherein the estimated melting temperature is calculated using the reference melting temperature.

2. A method for estimating a melting temperature ($T_m$) for a polynucleotide at a desired ion concentration [$X^+$], said polynucleotide having a known G-C content value, $f(G\text{-}C)$, comprising:
   (a) obtaining a reference melting temperature ($T_m^0$) for the polynucleotide, said reference melting temperature being a melting temperature obtained or provided for the polynucleotide at a reference ion concentration [$X^+$]$_0$; and
   (b) modifying the reference melting temperature by an amount, $$k(f(G-C)) \times \ln \frac{[X^+]}{[X^+]_0}$$

in which the coefficient $k(f(G\text{-}C))$ is a function of the G-C content value $f(G\text{-}C)$, wherein the estimated melting temperature is obtained by using the reference melting temperature.

3. The method of claim 2, wherein the coefficient k has a value determined by the relation $$k(f(G\text{-}C))=m \cdot f(G\text{-}C)+k_0;\text{ and}$$

wherein a first coefficient, m and a second coefficient, $k_0$, are optimized for predicting polynucleotide melting temperatures $T_m^0$.

4. The method of claim 2, wherein the reference melting temperature $T_m^0$ is used to calculate $T_m$ according to the formula:

$$T_m = T_m^0 + k \times \ln \frac{[X^+]}{[X^+]_0}.$$

5. The method of claim 4, wherein the coefficient k $$k(f(G\text{-}C))=m \cdot f(G\text{-}C)+k_0;$$

and wherein a first coefficient, m and a second coefficient, $k_0$ are optimized for predicting polynucleotide melting temperatures $T_m^0$.

6. The method of claim 2, wherein the reference melting temperature $T_m^0$ is used to calculate $T_m$ according to the formula:

$$T_m = T_m^0 + k(f(G-C)) \times \ln \frac{[X^+]}{[X^+]_0} + b \times (\ln^2[X^+] - \ln^2[X^+]_0)$$

wherein a coefficient b is optimized for predicting polynucleotide melting temperatures.

7. The method of claim 6, wherein k is $m \cdot f(G\text{-}C)+k_0$; and wherein a first coefficient, m, a second coefficient, $k_0$ and a third coefficient b are optimized for predicting polynucleotide melting temperatures $T_m^0$.

8. The method according to claim 5, wherein m is −3.22, $k_0$ is 6.39.

9. The method according to claim 7, wherein m is −4.62, $k_0$ is 4.52 and b=−0.985.

10. The method of claim 2, wherein the reference melting temperature $T_m^0$ is used to calculate $T_m$ according to the formula:

$$\frac{1}{T_m} = \frac{1}{T_m^0} + k(f(G-C)) \times \ln \frac{[X^+]}{[X^+]_0}.$$

11. The method of claim 10, wherein the coefficient k has a determined value by the relation $kf(G\text{-}C))=m \cdot f(G\text{-}C)+k_0$; and wherein a first coefficient, m and a second coefficient, $k_0$ are optimized for predicting polynucleotide melting temperatures.

12. The method of claim 2, wherein the melting temperature is obtained from the reference $T_m^0$ by utilizing the formula:

$$\frac{1}{T_m} = \frac{1}{T_m^0} + k(f(G-C)) \times \ln \frac{[X^+]}{[X^+]_0} + b \times (\ln^2[X^+] - \ln^2[X^+]_0)$$

wherein a coefficient b is optimized for predicting polynucleotide melting temperatures.

13. The method of claim 10, wherein k is $m \cdot f(G\text{-}C)+k_0$; and wherein a first coefficient, m and a second coefficient, $k_0$, and a third coefficient b are optimized for predicting polynucleotide melting temperature.

14. The method of claim 11, wherein $k_0$ is $-6.18 \times 10^{-5}$; m is $3.85 \times 10^{-5}$.

15. The method of claim 13, wherein $k_0$ is $-3.95 \times 10^{-5}$; m is $4.29 \times 10^{-1}$; and b is $9.40 \times 10^{-6}$.

16. The method of claim 2, wherein the G-C content value is the fraction of the polynucleotide's nucleotide bases that are either guanine or cytosine.

17. The method of claim 1, wherein the polynucleotide is DNA.

18. The method of claim 1, wherein the polynucleotide ranges in length from about 2 to about 500 basepairs.

19. The method of claim 1, wherein the polynucleotide ranges in length from about 5 to about 200 base pairs.

20. The method of claim 1, wherein the polynucleotide ranges from about 10 to about 30 basepairs in length.

21. The method of claim 1, wherein the reference melting temperature is experimentally determined.

22. The method of claim 1, wherein the reference melting temperature is calculated from a theoretical model.

23. The method of claim 1, wherein the reference melting temperature is obtained by utilizing a nearest neighbor model.

24. The method of claim 1, wherein the reference ion concentration is 1 M.

25. The method of claim 1, wherein the ion is a monovalent ion.

26. The method of claim 1, wherein the ion is selected from the group consisting of the cations of sodium, lithium, potassium, rubidium, cesium and francium.

27. The method of claim 1, wherein the desired ion concentration ranges between about 1 mM and about 5M.

28. The method of claim 1, wherein the desired ion concentration ranges between about 10 mM and about 2M.

29. The method of claim 1, wherein the desired ion concentration ranges between about 70 mM and about 1021 mM.

30. A computer system for predicting a melting temperature, which computer system comprises:

(a) a memory; and (b) a processor interconnected with the memory and having one or more software components loaded therein, wherein the one or more software components cause the processor to execute steps of a method according to claim 1.

31. A computer program product comprising a computer readable medium having one or more software components encoded thereon in computer readable form, wherein the one or more software components may be loaded into a memory of a computer system and cause a processor interconnected with said memory to execute steps of a method according to claim 1.

* * * * *

UNITED STATES PATENT AND TRADEMARK OFFICE
CERTIFICATE OF CORRECTION

PATENT NO. : 6,889,143 B2  
APPLICATION NO. : 10/660253  
DATED : May 3, 2005  
INVENTOR(S) : Mark Aaron Behlke et al.

It is certified that error appears in the above-identified patent and that said Letters Patent is hereby corrected as shown below:

Title page, item [73]  
Assignee:

Please delete "Intergrated DNA Technologies, Inc., Coralville, IN" and substitute -- Integrated DNA Technologies, Inc., Coralville IA --.

Signed and Sealed this

Twenty-seventh Day of February, 2007

JON W. DUDAS  
*Director of the United States Patent and Trademark Office*

SEQUENCE LISTING

<160> NUMBER OF SEQ ID NOS: 92

<210> SEQ ID NO 1
<211> LENGTH: 15
<212> TYPE: DNA
<213> ORGANISM: Artificial Sequence
<220> FEATURE:
<223> OTHER INFORMATION: oligonucleotide

<400> SEQUENCE: 1
tactaacatt aacta                                                   15

<210> SEQ ID NO 2
<211> LENGTH: 15
<212> TYPE: DNA
<213> ORGANISM: Artificial Sequence
<220> FEATURE:
<223> OTHER INFORMATION: oligonucleotide

<400> SEQUENCE: 2
atacttactg attag                                                   15

<210> SEQ ID NO 3
<211> LENGTH: 15
<212> TYPE: DNA
<213> ORGANISM: Artificial Sequence
<220> FEATURE:
<223> OTHER INFORMATION: oligonucleotide

<400> SEQUENCE: 3
gtacactgtc ttata                                                   15

<210> SEQ ID NO 4
<211> LENGTH: 15
<212> TYPE: DNA
<213> ORGANISM: Artificial Sequence
<220> FEATURE:
<223> OTHER INFORMATION: oligonucleotide

<400> SEQUENCE: 4
gtatgagaga cttta                                                   15

<210> SEQ ID NO 5
<211> LENGTH: 15
<212> TYPE: DNA
<213> ORGANISM: Artificial Sequence
<220> FEATURE:
<223> OTHER INFORMATION: oligonucleotide

<400> SEQUENCE: 5
ttctacctat gtgat                                                   15

<210> SEQ ID NO 6
<211> LENGTH: 15
<212> TYPE: DNA
<213> ORGANISM: Artificial Sequence
<220> FEATURE:
<223> OTHER INFORMATION: oligonucleotide

<400> SEQUENCE: 6
agtagtaatc acacc                                                   15

<210> SEQ ID NO 7
<211> LENGTH: 15

```
<212> TYPE: DNA
<213> ORGANISM: Artificial Sequence
<220> FEATURE:
<223> OTHER INFORMATION: oligonucleotide

<400> SEQUENCE: 7
atcgtctcgg tataa                                              15

<210> SEQ ID NO 8
<211> LENGTH: 15
<212> TYPE: DNA
<213> ORGANISM: Artificial Sequence
<220> FEATURE:
<223> OTHER INFORMATION: oligonucleotide

<400> SEQUENCE: 8
acgacaggtt tacca                                              15

<210> SEQ ID NO 9
<211> LENGTH: 15
<212> TYPE: DNA
<213> ORGANISM: Artificial Sequence
<220> FEATURE:
<223> OTHER INFORMATION: oligonucleotide

<400> SEQUENCE: 9
ctttcatgtc cgcat                                              15

<210> SEQ ID NO 10
<211> LENGTH: 15
<212> TYPE: DNA
<213> ORGANISM: Artificial Sequence
<220> FEATURE:
<223> OTHER INFORMATION: oligonucleotide

<400> SEQUENCE: 10
tggatgtgtg aacac                                              15

<210> SEQ ID NO 11
<211> LENGTH: 15
<212> TYPE: DNA
<213> ORGANISM: Artificial Sequence
<220> FEATURE:
<223> OTHER INFORMATION: oligonucleotide

<400> SEQUENCE: 11
accccgcaat acatg                                              15

<210> SEQ ID NO 12
<211> LENGTH: 15
<212> TYPE: DNA
<213> ORGANISM: Artificial Sequence
<220> FEATURE:
<223> OTHER INFORMATION: oligonucleotide

<400> SEQUENCE: 12
gcagtggatg tgaga                                              15

<210> SEQ ID NO 13
<211> LENGTH: 15
<212> TYPE: DNA
<213> ORGANISM: Artificial Sequence
<220> FEATURE:
<223> OTHER INFORMATION: oligonucleotide

<400> SEQUENCE: 13
```

-continued ggtccttact tggtg                                              15

<210> SEQ ID NO 14
<211> LENGTH: 15
<212> TYPE: DNA
<213> ORGANISM: Artificial Sequence
<220> FEATURE:
<223> OTHER INFORMATION: oligonucleotide

<400> SEQUENCE: 14
cgcctcatgc tcatc                                              15

<210> SEQ ID NO 15
<211> LENGTH: 15
<212> TYPE: DNA
<213> ORGANISM: Artificial Sequence
<220> FEATURE:
<223> OTHER INFORMATION: oligonucleotide

<400> SEQUENCE: 15
aaatagccgg gccgc                                              15

<210> SEQ ID NO 16
<211> LENGTH: 15
<212> TYPE: DNA
<213> ORGANISM: Artificial Sequence
<220> FEATURE:
<223> OTHER INFORMATION: oligonucleotide

<400> SEQUENCE: 16
ccagccagtc tctcc                                              15

<210> SEQ ID NO 17
<211> LENGTH: 15
<212> TYPE: DNA
<213> ORGANISM: Artificial Sequence
<220> FEATURE:
<223> OTHER INFORMATION: oligonucleotide

<400> SEQUENCE: 17
gacgacaaga ccgcg                                              15

<210> SEQ ID NO 18
<211> LENGTH: 15
<212> TYPE: DNA
<213> ORGANISM: Artificial Sequence
<220> FEATURE:
<223> OTHER INFORMATION: oligonucleotide

<400> SEQUENCE: 18
cagcctcgtc gcagc                                              15

<210> SEQ ID NO 19
<211> LENGTH: 15
<212> TYPE: DNA
<213> ORGANISM: Artificial Sequence
<220> FEATURE:
<223> OTHER INFORMATION: oligonucleotide

<400> SEQUENCE: 19
ctcgcggtcg aagcg                                              15

<210> SEQ ID NO 20
<211> LENGTH: 15
<212> TYPE: DNA
<213> ORGANISM: Artificial Sequence

```
<220> FEATURE:
<223> OTHER INFORMATION: oligonucleotide

<400> SEQUENCE: 20
gcgtcggtcc gggct                                                15

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
tatgtatatt ttgtaatcag                                           20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide

<400> SEQUENCE: 22
ttcaagttaa acattctatc                                           20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
tgattctacc tatgtgattt                                           20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
gagattgttt ccctttcaaa                                           20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
atgcaatgct acatattcgc                                           20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
ccactatacc atctatgtac                                           20
```

```
<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
ccatcattgt gtctacctca                                               20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
cgggaccaac taaaggaaat                                               20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
tagtggcgat tagattctgc                                               20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
agctgcagtg gatgtgagaa                                               20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
tacttccagt gctcagcgta                                               20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
cagtgagaca gcaatggtcg                                               20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide
```

```
<400> SEQUENCE: 33
cgagcttatc cctatccctc                                          20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
cgtactagcg ttggtcatgg                                          20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
aaggcgagtc aggctcagtg                                          20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
accgacgacg ctgatccgat                                          20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide

<400> SEQUENCE: 37
agcagtccgc cacaccctga                                          20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide

<400> SEQUENCE: 38
cagcctcgtt cgcacagccc                                          20

<210> SEQ ID NO 39
<211> LENGTH: 20
<212> TYPE: DNA
<213> ORGANISM: Artificial Sequence
<220> FEATURE:
<223> OTHER INFORMATION: oligonucleotide

<400> SEQUENCE: 39
gtggtgggcc gtgcgctctg                                          20

<210> SEQ ID NO 40
```

```
<211> LENGTH: 20
<212> TYPE: DNA
<213> ORGANISM: Artificial Sequence
<220> FEATURE:
<223> OTHER INFORMATION: oligonucleotide

<400> SEQUENCE: 40
gtccacgccc ggtgcgacgg                                              20

<210> SEQ ID NO 41
<211> LENGTH: 25
<212> TYPE: DNA
<213> ORGANISM: Artificial Sequence
<220> FEATURE:
<223> OTHER INFORMATION: oligonucleotide

<400> SEQUENCE: 41
gatatagcaa aattctaagt taata                                        25

<210> SEQ ID NO 42
<211> LENGTH: 25
<212> TYPE: DNA
<213> ORGANISM: Artificial Sequence
<220> FEATURE:
<223> OTHER INFORMATION: oligonucleotide

<400> SEQUENCE: 42
ataactttac gtgtgtgacc tatta                                        25

<210> SEQ ID NO 43
<211> LENGTH: 25
<212> TYPE: DNA
<213> ORGANISM: Artificial Sequence
<220> FEATURE:
<223> OTHER INFORMATION: oligonucleotide

<400> SEQUENCE: 43
gttctatact cttgaagttg attac                                        25

<210> SEQ ID NO 44
<211> LENGTH: 25
<212> TYPE: DNA
<213> ORGANISM: Artificial Sequence
<220> FEATURE:
<223> OTHER INFORMATION: oligonucleotide

<400> SEQUENCE: 44
ccctgcactt taactgaatt gttta                                        25

<210> SEQ ID NO 45
<211> LENGTH: 25
<212> TYPE: DNA
<213> ORGANISM: Artificial Sequence
<220> FEATURE:
<223> OTHER INFORMATION: oligonucleotide

<400> SEQUENCE: 45
taaccatact gaataccttt tgacg                                        25

<210> SEQ ID NO 46
<211> LENGTH: 25
<212> TYPE: DNA
<213> ORGANISM: Artificial Sequence
<220> FEATURE:
<223> OTHER INFORMATION: oligonucleotide

<400> SEQUENCE: 46
```

```
tccacacggt agtaaaatta ggctt                                              25

<210> SEQ ID NO 47
<211> LENGTH: 25
<212> TYPE: DNA
<213> ORGANISM: Artificial Sequence
<220> FEATURE:
<223> OTHER INFORMATION: oligonucleotide

<400> SEQUENCE: 47
ttccaaaagg agttatgagt tgcga                                              25

<210> SEQ ID NO 48
<211> LENGTH: 25
<212> TYPE: DNA
<213> ORGANISM: Artificial Sequence
<220> FEATURE:
<223> OTHER INFORMATION: oligonucleotide

<400> SEQUENCE: 48
aatatctctc atgcgccaag ctaca                                              25

<210> SEQ ID NO 49
<211> LENGTH: 25
<212> TYPE: DNA
<213> ORGANISM: Artificial Sequence
<220> FEATURE:
<223> OTHER INFORMATION: oligonucleotide

<400> SEQUENCE: 49
tagtatatcg cagcatcata caggc                                              25

<210> SEQ ID NO 50
<211> LENGTH: 25
<212> TYPE: DNA
<213> ORGANISM: Artificial Sequence
<220> FEATURE:
<223> OTHER INFORMATION: oligonucleotide

<400> SEQUENCE: 50
tggattctac tcaaccttag tctgg                                              25

<210> SEQ ID NO 51
<211> LENGTH: 25
<212> TYPE: DNA
<213> ORGANISM: Artificial Sequence
<220> FEATURE:
<223> OTHER INFORMATION: oligonucleotide

<400> SEQUENCE: 51
cggaatccat gttacttcgg ctatc                                              25

<210> SEQ ID NO 52
<211> LENGTH: 25
<212> TYPE: DNA
<213> ORGANISM: Artificial Sequence
<220> FEATURE:
<223> OTHER INFORMATION: oligonucleotide

<400> SEQUENCE: 52
ctggtctgga tctgagaact tcagg                                              25

<210> SEQ ID NO 53
<211> LENGTH: 25
<212> TYPE: DNA
```

-continued

```
<213> ORGANISM: Artificial Sequence
<220> FEATURE:
<223> OTHER INFORMATION: oligonucleotide

<400> SEQUENCE: 53
acagcgaatg gacctacgtg gcctt                                          25

<210> SEQ ID NO 54
<211> LENGTH: 25
<212> TYPE: DNA
<213> ORGANISM: Artificial Sequence
<220> FEATURE:
<223> OTHER INFORMATION: oligonucleotide

<400> SEQUENCE: 54
agcaagtcga gcagggccta cgttt                                          25

<210> SEQ ID NO 55
<211> LENGTH: 25
<212> TYPE: DNA
<213> ORGANISM: Artificial Sequence
<220> FEATURE:
<223> OTHER INFORMATION: oligonucleotide

<400> SEQUENCE: 55
gcgagcgaca ggttacttgg ctgat                                          25

<210> SEQ ID NO 56
<211> LENGTH: 25
<212> TYPE: DNA
<213> ORGANISM: Artificial Sequence
<220> FEATURE:
<223> OTHER INFORMATION: oligonucleotide

<400> SEQUENCE: 56
aaaggtgtcg cggagagtcg tgctg                                          25

<210> SEQ ID NO 57
<211> LENGTH: 25
<212> TYPE: DNA
<213> ORGANISM: Artificial Sequence
<220> FEATURE:
<223> OTHER INFORMATION: oligonucleotide

<400> SEQUENCE: 57
atgggtggga gcctcggtag cagcc                                          25

<210> SEQ ID NO 58
<211> LENGTH: 25
<212> TYPE: DNA
<213> ORGANISM: Artificial Sequence
<220> FEATURE:
<223> OTHER INFORMATION: oligonucleotide

<400> SEQUENCE: 58
cagtgggctc ctgggcgtgc tggtc                                          25

<210> SEQ ID NO 59
<211> LENGTH: 25
<212> TYPE: DNA
<213> ORGANISM: Artificial Sequence
<220> FEATURE:
<223> OTHER INFORMATION: oligonucleotide

<400> SEQUENCE: 59
gccaactccg tcgccgttcg tgcgc                                          25
```

<210> SEQ ID NO 60
<211> LENGTH: 25
<212> TYPE: DNA
<213> ORGANISM: Artificial Sequence
<220> FEATURE:
<223> OTHER INFORMATION: oligonucleotide

<400> SEQUENCE: 60
acgggtcccc gcaccgcacc gccag                                      25

<210> SEQ ID NO 61
<211> LENGTH: 30
<212> TYPE: DNA
<213> ORGANISM: Artificial Sequence
<220> FEATURE:
<223> OTHER INFORMATION: oligonucleotide

<400> SEQUENCE: 61
ttatgtatta agttatatag tagtagtagt                                 30

<210> SEQ ID NO 62
<211> LENGTH: 30
<212> TYPE: DNA
<213> ORGANISM: Artificial Sequence
<220> FEATURE:
<223> OTHER INFORMATION: oligonucleotide

<400> SEQUENCE: 62
attgatatcc ttttctattc atctttcatt                                 30

<210> SEQ ID NO 63
<211> LENGTH: 30
<212> TYPE: DNA
<213> ORGANISM: Artificial Sequence
<220> FEATURE:
<223> OTHER INFORMATION: oligonucleotide

<400> SEQUENCE: 63
aaagtacatc aacatagaga attgcatttc                                 30

<210> SEQ ID NO 64
<211> LENGTH: 30
<212> TYPE: DNA
<213> ORGANISM: Artificial Sequence
<220> FEATURE:
<223> OTHER INFORMATION: oligonucleotide

<400> SEQUENCE: 64
cttaagatat gagaacttca actaatgtgt                                 30

<210> SEQ ID NO 65
<211> LENGTH: 30
<212> TYPE: DNA
<213> ORGANISM: Artificial Sequence
<220> FEATURE:
<223> OTHER INFORMATION: oligonucleotide

<400> SEQUENCE: 65
ctcaacttgc ggtaaataaa tcgcttaatc                                 30

<210> SEQ ID NO 66
<211> LENGTH: 30
<212> TYPE: DNA
<213> ORGANISM: Artificial Sequence
<220> FEATURE:

<223> OTHER INFORMATION: oligonucleotide

<400> SEQUENCE: 66
tattgagaac aagtgtccga ttagcagaaa             30

<210> SEQ ID NO 67
<211> LENGTH: 30
<212> TYPE: DNA
<213> ORGANISM: Artificial Sequence
<220> FEATURE:
<223> OTHER INFORMATION: oligonucleotide

<400> SEQUENCE: 67
gtcatacgac tgagtgcaac attgttcaaa             30

<210> SEQ ID NO 68
<211> LENGTH: 30
<212> TYPE: DNA
<213> ORGANISM: Artificial Sequence
<220> FEATURE:
<223> OTHER INFORMATION: oligonucleotide

<400> SEQUENCE: 68
aacctgcaac atggagtttt tgtctcatgc             30

<210> SEQ ID NO 69
<211> LENGTH: 30
<212> TYPE: DNA
<213> ORGANISM: Artificial Sequence
<220> FEATURE:
<223> OTHER INFORMATION: oligonucleotide

<400> SEQUENCE: 69
ccgtgcggtg tgtacgtttt attcatcata             30

<210> SEQ ID NO 70
<211> LENGTH: 30
<212> TYPE: DNA
<213> ORGANISM: Artificial Sequence
<220> FEATURE:
<223> OTHER INFORMATION: oligonucleotide

<400> SEQUENCE: 70
gttcacgtcc gaaagctcga aaaggatac              30

<210> SEQ ID NO 71
<211> LENGTH: 30
<212> TYPE: DNA
<213> ORGANISM: Artificial Sequence
<220> FEATURE:
<223> OTHER INFORMATION: oligonucleotide

<400> SEQUENCE: 71
agtctggtct ggatctgaga acttcaggct             30

<210> SEQ ID NO 72
<211> LENGTH: 30
<212> TYPE: DNA
<213> ORGANISM: Artificial Sequence
<220> FEATURE:
<223> OTHER INFORMATION: oligonucleotide

<400> SEQUENCE: 72
tcggagaaat cactgagctg cctgagaaga             30

```
<210> SEQ ID NO 73
<211> LENGTH: 30
<212> TYPE: DNA
<213> ORGANISM: Artificial Sequence
<220> FEATURE:
<223> OTHER INFORMATION: oligonucleotide

<400> SEQUENCE: 73
cttcaacgga tcaggtagga ctgtggtggg                                    30

<210> SEQ ID NO 74
<211> LENGTH: 30
<212> TYPE: DNA
<213> ORGANISM: Artificial Sequence
<220> FEATURE:
<223> OTHER INFORMATION: oligonucleotide

<400> SEQUENCE: 74
acgcccacag gattaggctg gcccacattg                                    30

<210> SEQ ID NO 75
<211> LENGTH: 30
<212> TYPE: DNA
<213> ORGANISM: Artificial Sequence
<220> FEATURE:
<223> OTHER INFORMATION: oligonucleotide

<400> SEQUENCE: 75
gttattccgc agtccgatgg cagcaggctc                                    30

<210> SEQ ID NO 76
<211> LENGTH: 30
<212> TYPE: DNA
<213> ORGANISM: Artificial Sequence
<220> FEATURE:
<223> OTHER INFORMATION: oligonucleotide

<400> SEQUENCE: 76
tcagtaggcg tgacgcagag ctggcgatgg                                    30

<210> SEQ ID NO 77
<211> LENGTH: 30
<212> TYPE: DNA
<213> ORGANISM: Artificial Sequence
<220> FEATURE:
<223> OTHER INFORMATION: oligonucleotide

<400> SEQUENCE: 77
cgcgccacgt gtgatctaca gccgttcggc                                    30

<210> SEQ ID NO 78
<211> LENGTH: 30
<212> TYPE: DNA
<213> ORGANISM: Artificial Sequence
<220> FEATURE:
<223> OTHER INFORMATION: oligonucleotide

<400> SEQUENCE: 78
gacctgacgt ggaccgctcc tgggcgtggt                                    30

<210> SEQ ID NO 79
<211> LENGTH: 30
<212> TYPE: DNA
<213> ORGANISM: Artificial Sequence
<220> FEATURE:
<223> OTHER INFORMATION: oligonucleotide
```

```
<400> SEQUENCE: 79
gcccctccac tggccgacgg cagcaggctc                                30

<210> SEQ ID NO 80
<211> LENGTH: 30
<212> TYPE: DNA
<213> ORGANISM: Artificial Sequence
<220> FEATURE:
<223> OTHER INFORMATION: oligonucleotide

<400> SEQUENCE: 80
cgccgctgcc gactggagga gcgcgggacg                                30

<210> SEQ ID NO 81
<211> LENGTH: 10
<212> TYPE: DNA
<213> ORGANISM: Artificial Sequence
<220> FEATURE:
<223> OTHER INFORMATION: oligonucleotide

<400> SEQUENCE: 81
atcaatcata                                                      10

<210> SEQ ID NO 82
<211> LENGTH: 10
<212> TYPE: DNA
<213> ORGANISM: Artificial Sequence
<220> FEATURE:
<223> OTHER INFORMATION: oligonucleotide

<400> SEQUENCE: 82
ttgtagtcat                                                      10

<210> SEQ ID NO 83
<211> LENGTH: 10
<212> TYPE: DNA
<213> ORGANISM: Artificial Sequence
<220> FEATURE:
<223> OTHER INFORMATION: oligonucleotide

<400> SEQUENCE: 83
gaaatgaaag                                                      10

<210> SEQ ID NO 84
<211> LENGTH: 10
<212> TYPE: DNA
<213> ORGANISM: Artificial Sequence
<220> FEATURE:
<223> OTHER INFORMATION: oligonucleotide

<400> SEQUENCE: 84
ccaacttctt                                                      10

<210> SEQ ID NO 85
<211> LENGTH: 10
<212> TYPE: DNA
<213> ORGANISM: Artificial Sequence
<220> FEATURE:
<223> OTHER INFORMATION: oligonucleotide

<400> SEQUENCE: 85
atcgtctgga                                                      10

<210> SEQ ID NO 86
<211> LENGTH: 10
```

<212> TYPE: DNA
<213> ORGANISM: Artificial Sequence
<220> FEATURE:
<223> OTHER INFORMATION: oligonucleotide

<400> SEQUENCE: 86
agcgtaagtc                                                                    10

<210> SEQ ID NO 87
<211> LENGTH: 10
<212> TYPE: DNA
<213> ORGANISM: Artificial Sequence
<220> FEATURE:
<223> OTHER INFORMATION: oligonucleotide

<400> SEQUENCE: 87
cgatctgcga                                                                    10

<210> SEQ ID NO 88
<211> LENGTH: 10
<212> TYPE: DNA
<213> ORGANISM: Artificial Sequence
<220> FEATURE:
<223> OTHER INFORMATION: oligonucleotide

<400> SEQUENCE: 88
tggcgagcac                                                                    10

<210> SEQ ID NO 89
<211> LENGTH: 10
<212> TYPE: DNA
<213> ORGANISM: Artificial Sequence
<220> FEATURE:
<223> OTHER INFORMATION: oligonucleotide

<400> SEQUENCE: 89
gatgcgctcg                                                                    10

<210> SEQ ID NO 90
<211> LENGTH: 10
<212> TYPE: DNA
<213> ORGANISM: Artificial Sequence
<220> FEATURE:
<223> OTHER INFORMATION: oligonucleotide

<400> SEQUENCE: 90
gggaccgcct                                                                    10

<210> SEQ ID NO 91
<211> LENGTH: 11
<212> TYPE: DNA
<213> ORGANISM: Artificial Sequence
<220> FEATURE:
<223> OTHER INFORMATION: oligonucleotide

<400> SEQUENCE: 91
cgtacacatg c                                                                  11

<210> SEQ ID NO 92
<211> LENGTH: 11
<212> TYPE: DNA
<213> ORGANISM: Artificial Sequence -continued

```
<220> FEATURE:
<223> OTHER INFORMATION: oligonucleotide

<400> SEQUENCE: 92
ccattgctac c                                                        11
```